United States Patent
Polsky

(10) Patent No.: US 8,034,141 B2
(45) Date of Patent: Oct. 11, 2011

(54) DYNAMIC BARRIER ISOLATION CHAMBER

(76) Inventor: Robert H. Polsky, Plymouth Meeting, PA (US)

( * ) Notice: Subject to any disclaimer, the term of this patent is extended or adjusted under 35 U.S.C. 154(b) by 470 days.

(21) Appl. No.: 12/229,568

(22) Filed: Aug. 25, 2008

(65) Prior Publication Data
US 2009/0061751 A1 Mar. 5, 2009

Related U.S. Application Data

(63) Continuation-in-part of application No. 10/764,791, filed on Jan. 23, 2004, now abandoned.

(51) Int. Cl.
*B01D 46/00* (2006.01)

(52) U.S. Cl. ............................ 55/385.2; 312/1; 454/187

(58) Field of Classification Search ............... 55/385.2, 55/310, 419, 467, 470, 473; 95/12, 22, 25, 95/45, 273; 454/187, 236, 344; 600/21; 422/48, 300
See application file for complete search history.

(56) References Cited

U.S. PATENT DOCUMENTS

| | | | | |
|---|---|---|---|---|
| 5,216,560 | A | * | 6/1993 | Brug et al. ............... 360/327.33 |
| 5,730,765 | A | * | 3/1998 | Henry et al. .................... 96/420 |
| 5,730,777 | A | * | 3/1998 | Petersen et al. .................. 95/12 |
| 2006/0150593 | A1 | * | 7/2006 | Ono .............................. 55/413 |

* cited by examiner

*Primary Examiner* — Duane Smith
*Assistant Examiner* — Minh-Chau Pham

(57) ABSTRACT

The invention concerns an isolation chamber for isolating substances from the ambient while simultaneously maintaining aseptic conditions within the isolation chamber and protecting the operator from potent compounds. The isolation chamber comprises a first container surrounding and defining an isolation space of holding the substances and a second container surrounding the first container. Preferably, the pressure of the isolation space is lower than the pressure of the barrier space.

5 Claims, 19 Drawing Sheets

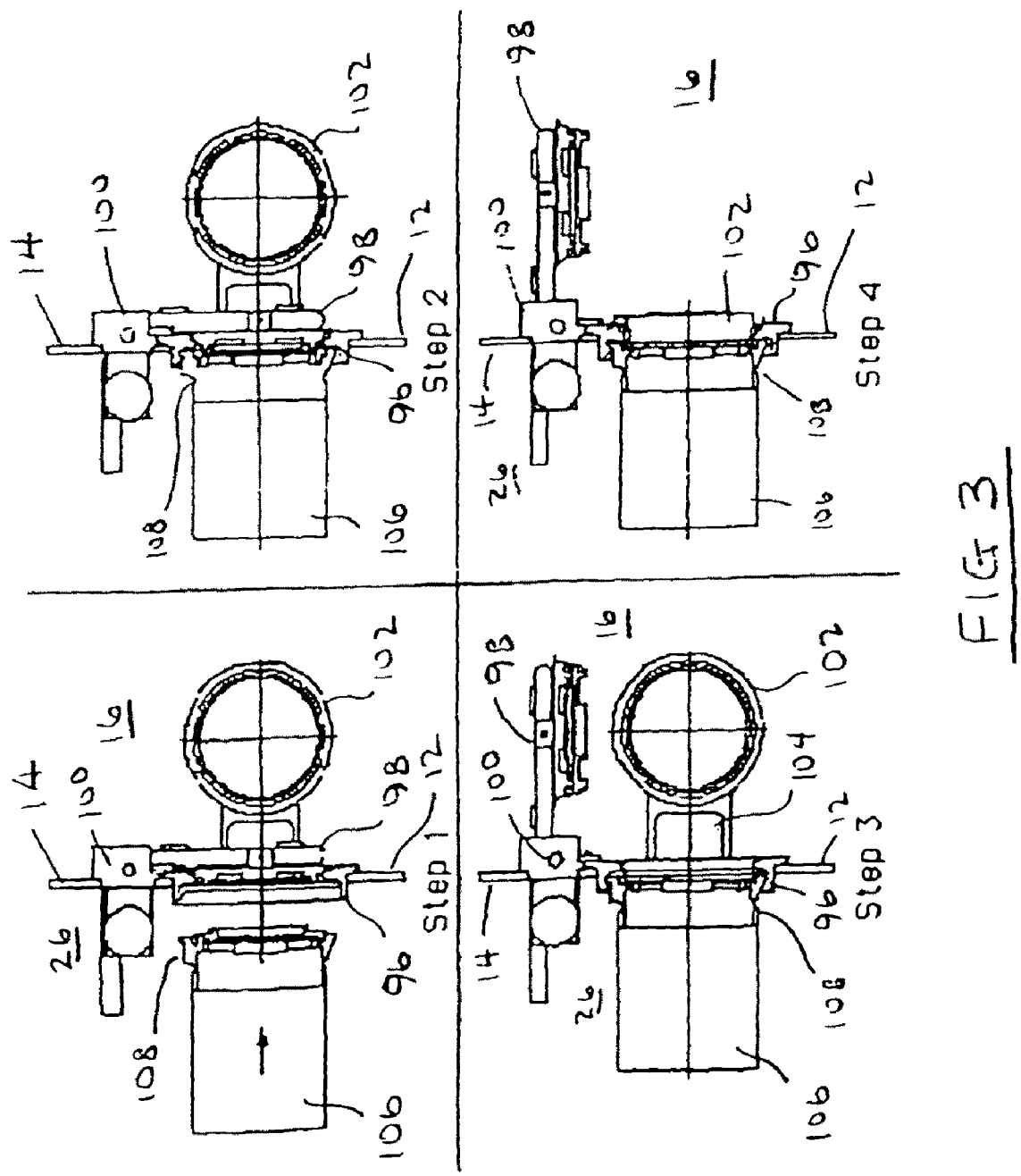

DYNAMIC BARRIER ISOLATION CHAMBER

CROSS REFERENCE TO RELATED APPLICATIONS

The present application is a Continuation in Part (CIP) of application Ser. No. 10/764,791 now abandoned and claims the benefits under all relevant U.S. statutes, including the benefit of priority under 35 U.S.C. §120.

The present application claims the benefits under all relevant U.S. statutes, including the benefit of priority under 35 U.S.C. §119(c), to U.S. Provisional Application No. 60/422,028 filed Jan. 23, 2003, titled DYNAMIC BARRIER ISOLATION CHAMBER in the name of Robert H. Polsky. U.S. Provisional Application No. 60/422,028, filed Jan. 23, 2003, is hereby incorporated by reference as if fully set forth herein.

FIELD OF THE INVENTION

The present invention relates generally to chambers for establishing and maintaining a space isolated from the ambient, for example, for the handling and manufacture of potent aseptic and/or hazardous compounds or for treatment of injured personnel subject to infection, as well as personnel having infectious diseases.

BACKGROUND OF THE INVENTION

Containment: When handling extremely hazardous compounds such as cytotoxins, carcinogens, mutagens as well as biological and nerve agents for experiment and/or manufacture, it is necessary to isolate the hazardous compounds from the workers handling them. Proper containment of such compounds from the ambient using a containment chamber that allows workers to handle extremely hazardous compounds in a laboratory or manufacturing environment without the need for extensive and uncomfortable personal protective equipment in the form of respirators and full body suits. Such containment chambers typically have means, such as sealed gloves, robotic manipulators, air locks and the like allowing operators to manually or remotely handle laboratory apparatus and other equipment as necessary for experimentations and manufacture of the hazardous compounds.

Isolation: Effective isolation in the handling of compounds (both hazardous and non hazardous) in an aseptic environment may be necessary for their development, formulation and manufacture. Such compounds are used to treat diseases by injection into the blood stream and must not contain any pyrogens which may cause infection.

It is also useful to have the ability to isolate individuals or animals from the ambient while providing them with medical treatment or transporting them from a crisis scene or between medical facilities. Isolation of individuals in portable or permanently fixed chambers may be necessary to protect health care workers from infectious diseases or dangerous toxins with which the individuals are infected or contaminated or to protect the individual from infection from the healthcare workers, as well as airborne viruses and germs. Such isolations during transport may be critical to the survival of, for example, burn victim who are particularly susceptible to infection, as well as anyone whose immune system has been compromised, such as those having HIV or undergoing chemotherapy.

It is desirable that the chambers provide for extremely low operator exposure limits to the hazardous compounds or low patient exposure limits to airborne contaminants, depending upon the particular application. Depending on the hazardous compound at issue, exposure limit requirements for current chambers may be in the microgram (millionth of a gram) range or smaller for an eight hour period of exposure. These are extremely small limits and it is not always possible to achieve and maintain such levels with the conventional isolation chambers. Being mechanical devices, the conventional isolation chambers suffer from a host of malfunctions allowing leakage including seepage at joints, imperfections, flaws, fissures or fractures of the chamber walls, permeation due to age, seal wear and tear, component failure due to normal usage, wear and tear, accidental puncture, pressure rupture or chemical erosion, as well as operator errors including importer use such as failure to close doors or air locks so that they seal properly.

Current isolation chambers are particularly inadequate for handling aseptic cytotoxins such as those compounds used in cancer therapy. Such compounds must be reliably contained within the chamber to safeguard the lives of those working with them, yet must also be isolated from airborne pyrogens in the ambient. For safety reasons, chambers holding aseptic cytotoxins are maintained at either a reduced internal pressure so that in the event of a leak, a puncture or other breach in the integrity of the chamber walls or seals, the cytotoxins will not escape form the chamber and contaminate the ambient, or at an elevated pressure to satisfy FDA concerns regarding aseptic environments. However, in the event of a breach or leak, ambient air will be drawn into the chamber, bringing airborne pyrogens with it which will contaminate the aseptic cytotoxins/system rendering them unusable for experiment or treatment. In the later case of elevated internal pressure, it is common to respond to barrier leaks/failure by rapidly switching to reduced internal pressure which then results in a compromised aseptic system. For reduced internal pressure containment systems that default to reduced internal pressure, post failure shutdown is addressed by people garbed in personal protection equipment (PPE) to a level appropriate to the potential hazard. PPE could reasonably be a full body suit sealed with dedicated air line or SCBA. The isolator and the entire room must be decontaminated in a relatively complex and expensive exercise prior to being cleaned, repaired and reused. The loss of one or more batches of aseptic cytotoxins during manufacturing or research becomes unacceptably expensive and yet a failsafe isolation chamber is virtually required due to the mortal risk posed to laboratory technicians and manufacturing personnel. There is clearly a need for an isolation chamber which fails safely by not permitting egress of hazardous substances from the chamber yet also prevents ingress of airborne contaminants.

SUMMARY OF THE INVENTION

The invention concerns an isolation chamber for isolating substances from the ambient. The isolation chamber includes a first container surrounding and defining an isolation space for holding the substances and a second container surrounding the first container. A barrier space, containing an elevated pressure, with respect to the isolation space and ambient, dynamic fluid barrier, is positioned between the first and second containers. A first fluid intake duct is associated with the first container and a second fluid intake duct is associated with the second container. The intake ducts provide fluid communication between the ambient, the barrier space and the isolation space. An intake filter is associated with the second intake duct for filtering fluid passing from the ambient into the barrier and isolation spaces. A first fluid exhaust duct is associated with the first container and a second fluid exhaust duct is associated with the second container, the exhaust ducts providing fluid communication between the isolation space and the ambient and the barrier space and the ambient. An exhaust filter is associated with the first exhaust duct for filtering fluid passing from the isolation space to the ambient. A fluid pump is associated with one of the intake and exhaust ducts for moving fluid from the ambient through the isolation space and the barrier space and back to the ambient.

Preferably, fluid pressure within the isolation space is less than fluid pressure within the barrier space.

The elevated fluid pressure within the barrier space, while controllable by an operator or other design criteria, is fundamentally governed by the laws of Newtonian physics such that any breach or breaches in any confining materials, such as an isolator wall or walls, will immediately be responded to by the driving force of the fluid within the barrier space, or multi-walled isolation device barrier space, such that the fluid at elevated pressure within the barrier space will proactively seek a lesser energy level, or the lower pressure environments. A fluid at an elevated pressure within the barrier, entering and passing through said breaches will automatically simultaneously act to "fill" the breach thus preventing fluids or particles at lower energies or pressure environments to enter the barrier space, therefore, by default, simultaneously protecting an aseptic high potency, high value compound within the isolator without compromising the operator or ambient environment and continuously maintaining the clean aseptic integrity of the barrier space, allowing for a continuously clean process environment, clean and controlled shutdown, and continuously aseptic isolation of high value aseptic potent compounds. The dynamic barrier isolation chamber fluid is defined as any fluid. This therefore includes fluidized material suitable for maintaining a fluid barrier within multi walled isolation or barrier systems. These barrier fluids are generally identified as traditional gases and liquids at standard temperature and pressure, super cooled liquids, molten liquids, plasmas or combinations thereof as required by the isolation system dynamic fluid barrier service requirements. Service requirements for the dynamic barrier fluid may be traditionally defined in terms of pressure, density, molecular weight, phase, viscosity, temperature, clarity, or ability to accommodate a marker.

A further example of dynamic fluid or fluidized barriers are a fluidization of chemically active particles such as cement, or chemically or electrically active particles or particles catalytically active such that when entering a breach the particles become chemically, or electrostatically, or otherwise physically active and cement, coagulate, fuse, causing an obstruction in the barrier wall thus plugging the breach.

The barrier fluids have the ability to accommodate a marker for potential leak tracing.

The Dynamic Barrier Isolation Chamber is not intended to have the dynamic fluid barrier operate at reduced pressure.

The flow splitters, depicted in the original application, provide a single perforation simultaneously into the interior and exterior isolator shell materials, designed to simultaneously control pressures within the isolation chamber and the barrier space.

BRIEF DESCRIPTION OF THE DRAWINGS

The accompanying drawings, which are incorporated in and form a part of the specification, illustrate the embodiments of the present invention and, together with the following description, serve to explain the principles of the invention. For the purpose of illustrating the invention, there are shown in the drawings embodiments which are presently preferred, it being understood, however, that the invention is not limited to the specific instrumentality or the precise arrangement of elements or process steps disclosed.

In the drawings:

FIG. 2 is a perspective view of transfer port used with the isolation chamber shown in FIG. 1;

DETAILED DESCRIPTION OF THE PREFERRED EMBODIMENT

In describing a preferred embodiment of the invention, specific terminology will be selected for the sake of clarity. However, the invention is not intended to be limited to the specific terms so selected.

Figure 1:
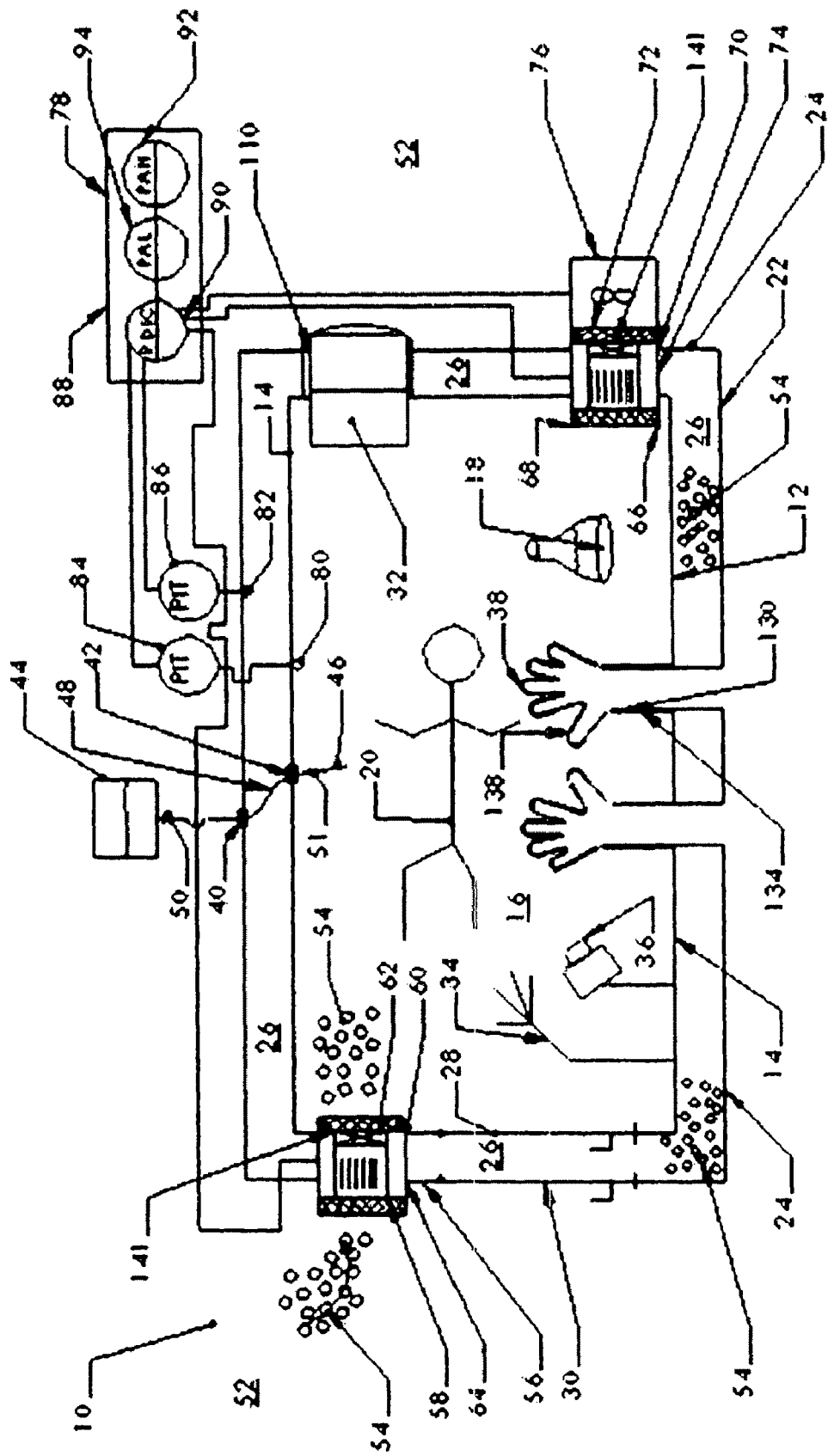
FIGS. 1 and 1A are schematic views of an isolation chamber according to the invention.

FIG. 1 shows a dynamic barrier isolation chamber 10 according to the invention. Chamber 10 has an inner container 12, preferably gas tight, and formed of a plurality of interconnected sidewalls 14. Sidewalls 14 surround and define an isolation space 16 for receiving the items or individuals to be isolated for handling, treatment or transport. If the chamber 10 is intended for use handling dangerous compounds 18, such as aseptic cytotoxins, nerve agents, biological agents and the like, these compounds are received within the isolation space 16 for experiment or manufacture. Alternatively, chamber 10 may be designed to isolate an individual 20 for medical treatment, the individual being received within the isolation space 16. Although two uses of chamber 10 are both represented in FIG. 1, this is for economy of illustration and by way of example only and does not require or imply that the chamber 10 need be of dual use in this manner or limited to the uses herein described. It is preferred that chambers 10 in according to the invention will be designed and equipped in detail for a specific use, the common feature of all the chambers designed according to the invention, regardless of their intended use, being the way in which the chamber is constructed and operated to maintain the isolation space 16 isolated from the ambient as further described below.

Inner container 12 is surrounded by an outer container 22, also preferably gas tight and formed of a plurality of interconnected sidewalls 24. A barrier space 26 is established between the respective sidewalls 14 and 24 of the inner and outer containers 12 and 22. Access to the isolation space 16 is provided by one or more doors such as 28 and 30, positioned in facing sidewalls 14 and 24 of the inner and outer containers 12 and 22. doors 28 and 30 are substantial in size and are designed to provide a gas tight seal when closed but open to allow relatively large items such as the patient 20 or laboratory apparatus, compound samples 18 and the like to be placed within the isolation space 16 prior to sealing the chamber and performing intended activities such as medical treatment, experimentation or manufacture of the compound requiring isolation. Further access to the isolation space 16 is provided by a transfer port 32, which operates as an airlock to permit items to be introduced and removed into and from the isolation space when the chamber is sealed up and operating without contaminating the isolation space 16, the barrier space 26 or the ambient. A detailed description of the transfer port is provided below.

The chamber is equipped with any of various devices allowing operators or health care workers to manipulate items within the isolation space. Such devices are generally known and comprise, for example, remote robotic manipulator arms 34, television camera 36, and flexible gloves 38. Gloves 38 are part of the dynamic barrier system and are described in detail below. The chamber 10 may also have external ports 40 on the outer container 22 which allow access to the isolation space 16 through sidewalls 24 and 14 providing services such as electrical power, running water, pressurized gas and the like which may be used within the chamber. The external ports 40 are associated with corresponding ports 42 on the inner container 12 to allow access to the externally provided services in the isolation space 16. By way of example, an intravenous fluid bag 44 is shown engaging an external port 40, the bag 44 being connected to an intravenous needle 46 attached to the corresponding associated internal port 42 for use with the patient 20. The ports such as 40 and 42 are sealed with the sidewalls to prevent leakage from either the isolation space 16 or the barrier space 26. for ports intended to pass fluids such as liquids and gases through the container sidewalls 14 and 24 the lines 48 are connecting the ports and the various pieces of apparatus such as the intravenous bag 44 an the needle 46 have two check valves 50 and 51. Check valve 50 is located outside chamber 10, and check valve 51 is located within the isolation space 16. The check valves 50 and 51 allow fluid flow only into the chamber 10 and close automatically to prevent back flow of the isolation space 16 or the barrier space 26.

The dynamic barrier which ensures that contaminants do not enter the isolation space 16 or that dangerous substances do not escape there-from to the ambient 52 is formed by controlling the flow and pressure of a barrier gas 54 through and within the barrier space 26 and the inner container 12. Barrier gas 54 is preferably ambient air, but could also be pressurized air, custom mixtures of gases or single gases such as nitrogen or helium to provide an inert atmosphere within the chamber 10 as required. The dynamic barrier is further described as an elevated pressure fluid curtain in the form of a dynamic fluid barrier defined by density, molecular weight, phase, fluid viscosity, temperature, pressure, clarity, a fluid with a density between 0.089 g/l but less than 13.5 g/cm$^3$ is envisioned as preferred, a fluid with a molecular weight between 1.008 g/mole and 200.58 g/mole is envisioned as preferred, a fluid in a gas or liquid phase is envisioned as preferred, a fluid with a viscosity between 8.4×10$^{-6}$ Pa s but less than 250,000 cP, including both Newtonian and non-Newtonian character, is envisioned as preferred, a fluid with a temperature between 1 degree Kelvin but less than 475 Kelvin is envisioned as preferred, a fluid with a pressure between −30 inches Hg but less than 50 psi is envisioned as preferred, a clear and colorless fluid, capable of being loaded with a color or turbidity marker is envisioned as preferred to facilitate leak location.

To facilitate gas flow through the chamber 10, the outer container 22 has an external intake port 56 extending through its sidewall 24 and fitted with an intake filter 58. All of the gas filters used within chamber 10 are high efficiency particle filters or their equivalent, and capable of removing particles down to 0.12 microns in size from the incoming air. A corresponding internal intake port 60 also having a particle filter 62 further filtering the air entering the isolation space 16. A flow splitting and regulating device 64 provides fluid communication between the external intake port 56, the barrier space 26 and the internal intake port 60. Flow splitter 64 is adjustable to separately control the relative flow of volume of barrier gas 54 into the barrier space 26 and the isolation space 16. Details of the operation of flow splitter 64 are provided below.

Inner container 12 is fitted with an internal exhaust port 66 extending through its sidewall 14. Again, an exhaust filter 68 is associated with the internal exhaust port to filter barrier gas 54 exiting the isolation space 16. Exhaust filter 68 ensures no harmful compounds escape with the barrier gas. An external exhaust port 70 extends through sidewall 24 of the outer container 22. External exhaust port 70 also has a high efficiency particle filter 72 filtering the barrier gas 54 to prevent escape of harmful compounds into ambient. A flow combining and regulating device 74 provides fluid communication between the internal exhaust port 66 and the external exhaust port 70. Flow combiner 74 combines the flow of barrier gas 54 from the isolation space 16 with the flow from the barrier space 26 and regulates the relative volume of flow from these spaces through the external exhaust port 70 and into the ambient 52.

Preferably, the barrier gas 54 is drawn through both the barrier space 26 and the isolation space 16 by an induction blower 76 associated with the external exhaust port 70. Other means for ensuring flow of barrier gas 54 through the chamber are also feasible, for example via forced air blowers, air pumps, compressors or by compressed gas from a reservoir, the reservoir being useful when custom gases or inert atmospheres are required within the chamber 10.

A control system 78 is used to control the flow splitter 64, the flow combiner 74 and the blower 76 to regulate the flow and pressure of barrier as 54 within the chamber 10. control system 78 includes pressure sensors 80 and 82 respectively mounted in the isolation space 16 and the barrier space 26 to monitor the pressure of barrier gas 54 in these spaces. Pressure sensors 80 and 82 are in communication with respective pressure indicator transmitters 84 and 86 which relay signals from the sensors indicative of the respective pressures within the spaces to a control device 88, preferably a microprocessor based computer. Control device 88 comprises a pressure differential indicator and component controller 90 which receives and interprets the signals from the pressure sensors 80 and 82. The pressure differential indicator and component controller 90 is in communication with the blower 76, the flow combiner 74 and the flow splitter 64. in response to the received signals from the pressure sensors 80 and 82 and according to a programmed algorithm, preferably resident in the control device 88, the component controller 90 adjusts the operation of each named component (the blower 76, the flow combiner 74 and the flow splitter 64) so that the pressure of the barrier gas 54 within the isolation space 16 is constantly maintained within a predetermined range and below the pressure of the barrier gas 54 within the barrier space 26, which is also maintained within a predetermined range. The control system 88 also includes high and low pressure alarms 92 and 94 which provide alarm signals to an operator of the chamber indicating barrier gas pressure out of the desired range in either the isolation space 16 or the barrier space 26. such alarms are useful to indicate a malfunction of the chamber 10, which could, for example, be a leak in one or both of the containers 12 and 22, a failure of the flow splitter 64, the flow combiner 74, the induction blower 76, the doors 28 and 30, as well as the transfer port 32. Details of the control system operation are provided below.

This invention may be configured with a closed loop or semi-closed loop fluid system to conserve expensive gas mixtures or to undergo burning analysis or capture.

Chamber 10 is further equipped with transfer port 32, shown schematically in FIG. 1. Transfer ports providing safe access for the transfer of items to and from a sealed chamber while maintaining isolation of the chamber and the items from the ambient are known and used throughout the pharmaceutical and medical industry as well as in the manufacture of integrated circuits. An example of a transfer port developed by Central Research Laboratories and useable with the chamber 10 is provided in FIG. 2, which shows the transfer port 32 as seen from inside the isolation space 16.

Transfer port 32 comprises a flange 96 mounted in the sidewall 14 of the inner container 12. A door 98 sealingly mates with flange 96 to close the transfer port 32, the door 98 being preferably hingedly mounted to open inwardly into the inner container 12. The door 98 may be remotely opened and closed by means of an actuator 100 under the control of control system 78. A protective collar 102 is also hingedly mounted to pivot for engagement with the flange 96 when the door 98 is open. Like door 98, collar 102 is described below.

Figure 3:
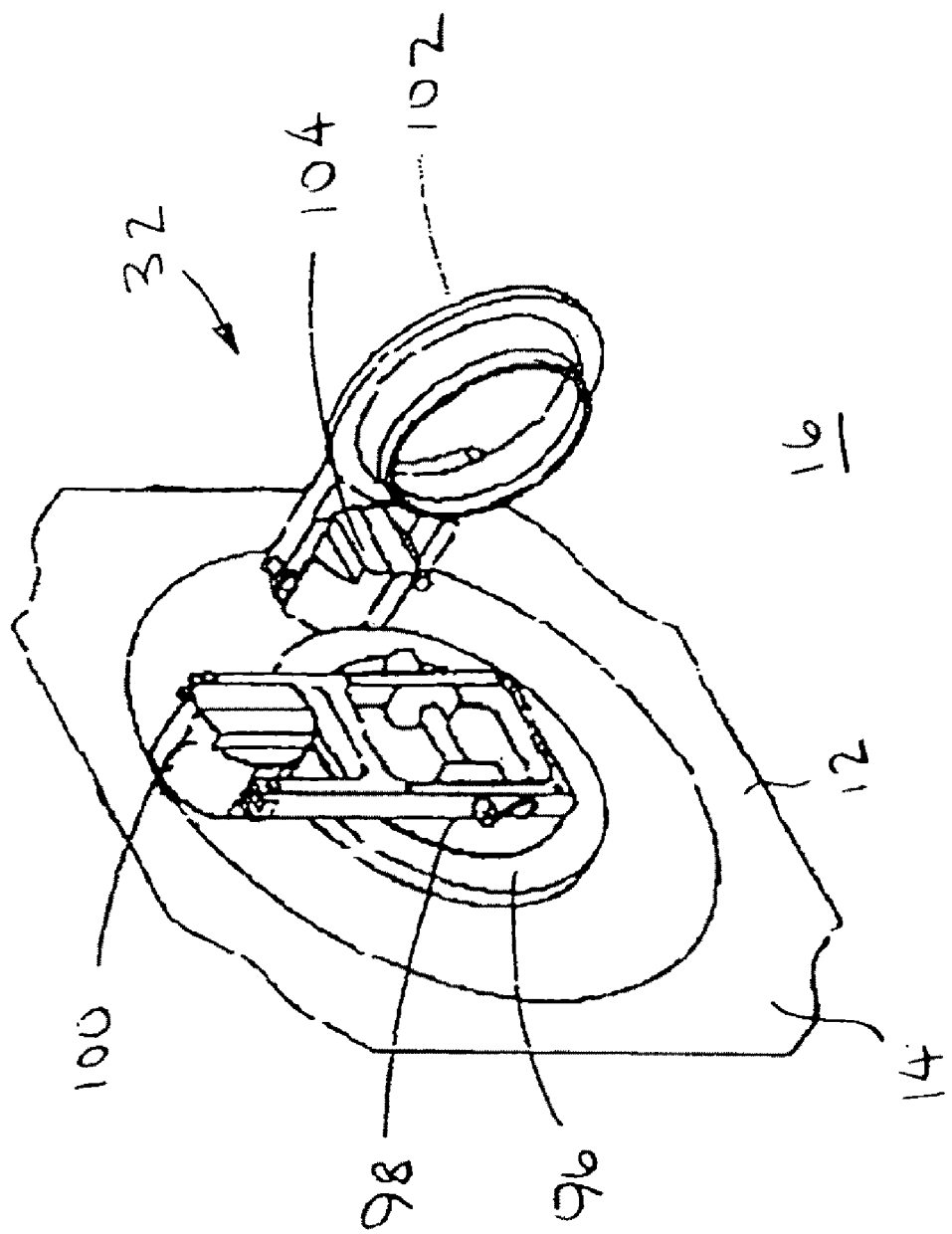
FIG. 3 illustrates the operation of the transfer port shown in FIG. 2 in a series of steps.

FIG. 3 shows how transfer port 32 operates to effect transfer of a hazardous substance to the sealed chamber 10. As shown in Step 1 of the Figure, the hazardous substance is held within a sealed transfer canister 106 which is brought into alignment with flange 96 on the outside of inner container 12. As shown in Step 2, the canister 106 is sealingly engaged with the flange 96. Sterilizing means (not shown) are provided in flange 96 so that the portion of transfer canister 106 that faces the door 98 is sterilized and any potential contaminants rendered harmless. Heat sterilization is preferred. After sterilization, as shown in Step 3, door 98 is opened by actuator 100 and the sealed lid (not shown) of canister 106 may be manually removed or opened by an operator for access to the interior of the canister from the isolation space 16. As shown in Step 4, the protective collar 102 is pivoted into position covering flange 96, as well as components of the canister 106. The collar protects the interface between the canister 106 and the transfer port 32 and shields the operator, working though glove within the chamber, from any residual hot surfaces resulting form the sterilization step.

As shown in FIG. 1, the transfer port 32 is located within the sidewall 14 of the inner container 12. Access to the transfer port 32 must be provided through the sidewall 24 of the outer container 22. For the barrier system to work as intended, it is necessary to be able to isolate the transfer port 32 from the barrier space 26 when the door 98 is open, yet allow barrier gas 54 into the barrier space 26 adjacent to the transfer port 32. This is accomplished by surrounding the transfer port 32 with a valved isolation collar 110, shown in detail in FIGS. 4-7.

Figure 4:
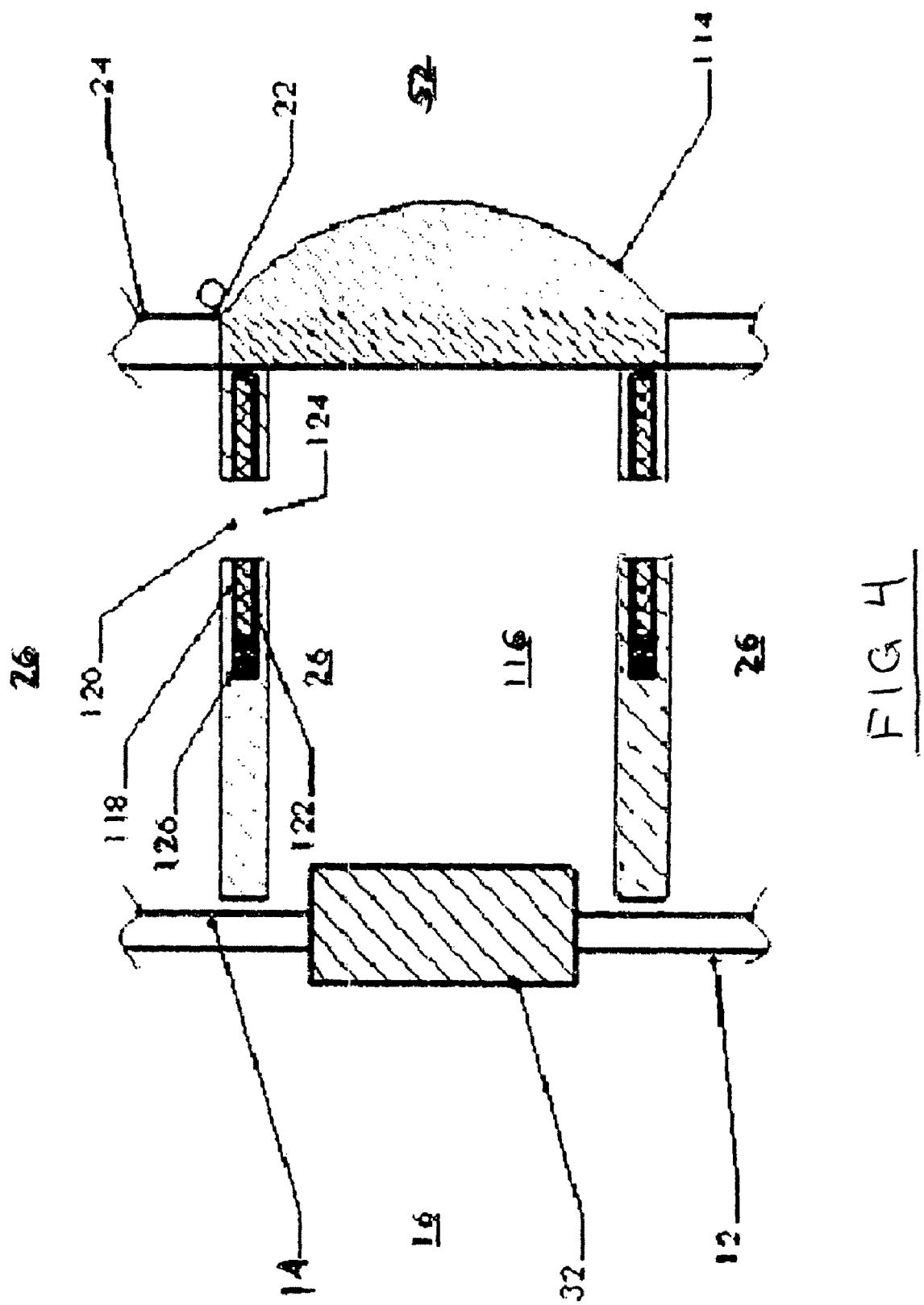
FIG. 4 is a cross sectional view of a component used with the isolation chamber shown in FIG. 1.
Figure 5:
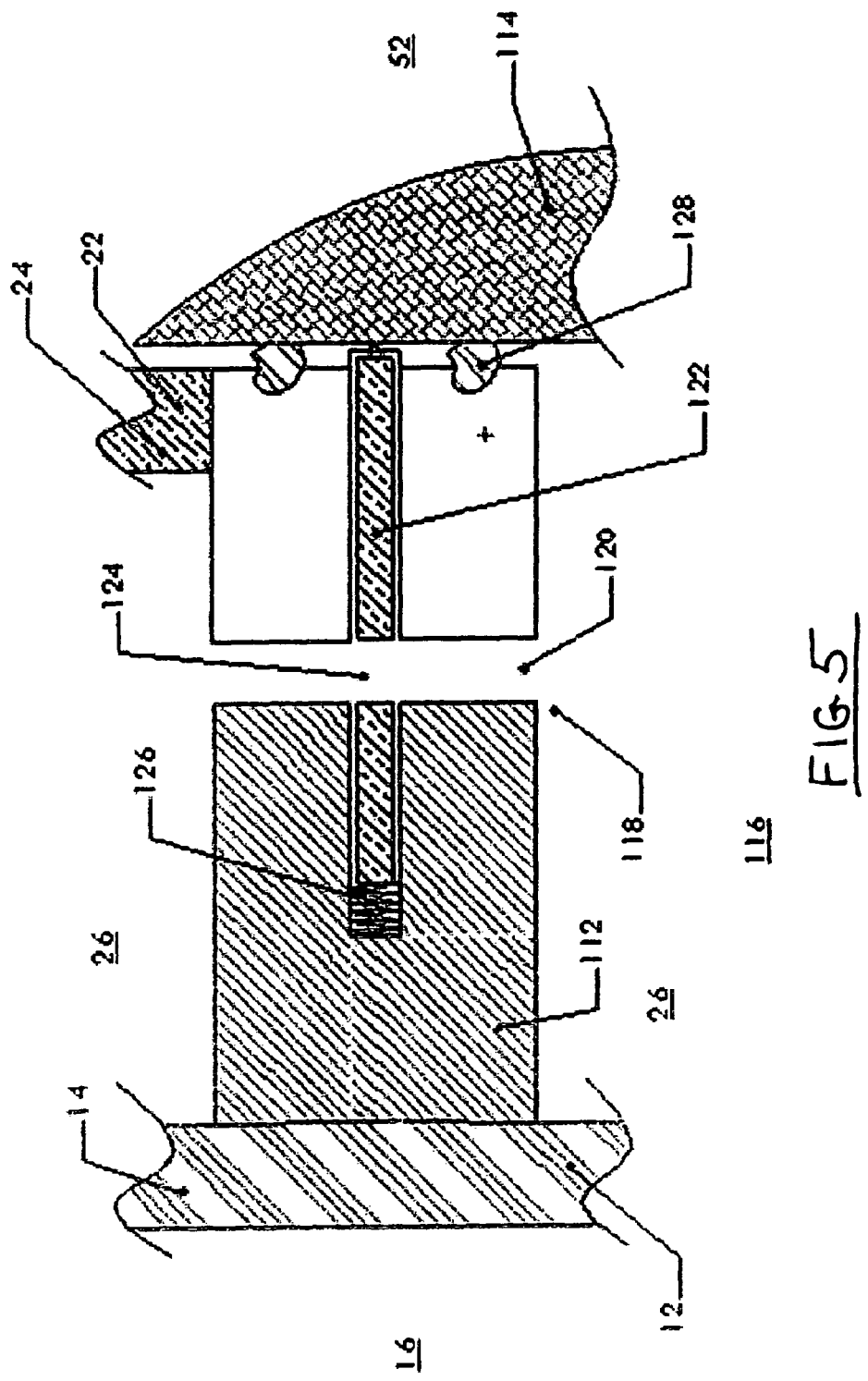
FIGS. 5-7 are partial views of the component shown in FIG. 4 illustrating its operation.
Figure 6:
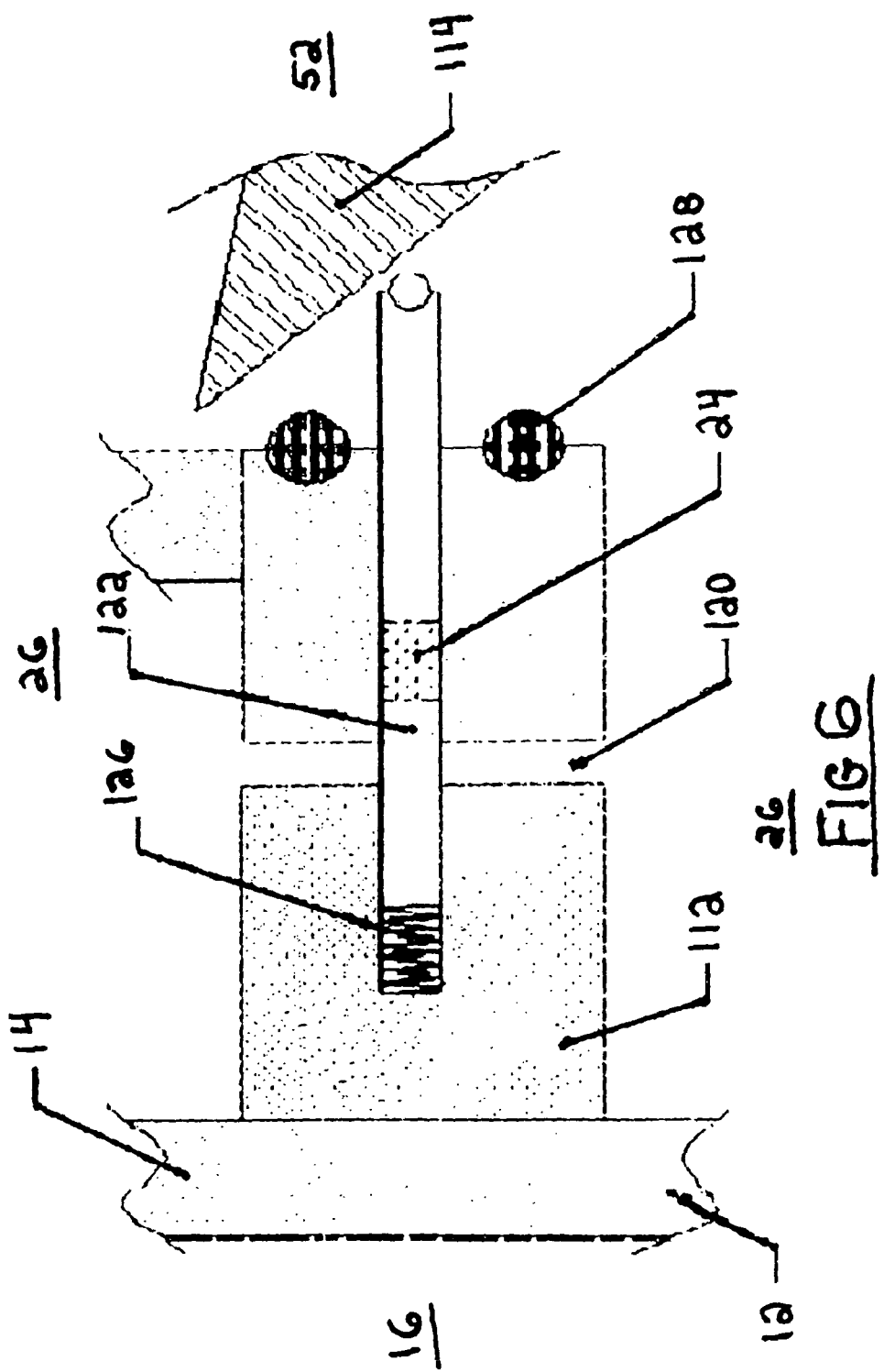

As shown in FIG. 4, isolation collar 110 includes a plenum 112 traversing barrier space 26 and sealingly engaging the inner and outer containers 12 and 22. A plenum door 114 mounted on the outer container 22 sealingly closes the plenum, isolating its interior 116 from the ambient 52. The plenum 112 has one or more valves 118 which provide fluid communication between the plenum interior 116 and the barrier space 26. As shown in FIG. 4, the valves 118 are open when door 114 is closed, and the plenum interior may thus be considered part of the barrier space 26. When door 114 is open, the valves 118 close, thus isolating the plenum interior 11 from the barrier space 26. By way of example, FIG. 5 shows a particular embodiment of a valve 118. The valve comprises a port 120 through the plenum 112. A valve closing member 122 is mounted on the plenum 112 in overlying relation with port 120. The valve closing member 122 has an opening 124 which is aligned with the port 120 when the door 114 is closed; the vale 118 being open. As shown in FIG. 6, the closing member 122 I movable in response to the opening of door 114, preferably by a biasing spring 126 which biases the valve closing member 122 against door 11. When the door is opened, the biasing spring moves the valve closing member 122 outwardly, forcing the opening 124 out of alignment with port 120, thereby closing valve 118. Similarly, closing the door 114 opens the valve 118 by moving the opening 124 in the valve closing member 122 back into alignment with the port 120. When closed, the door 114 engages seals 128 which seal the plenum interior 116 from the ambient 52.

Figure 7:
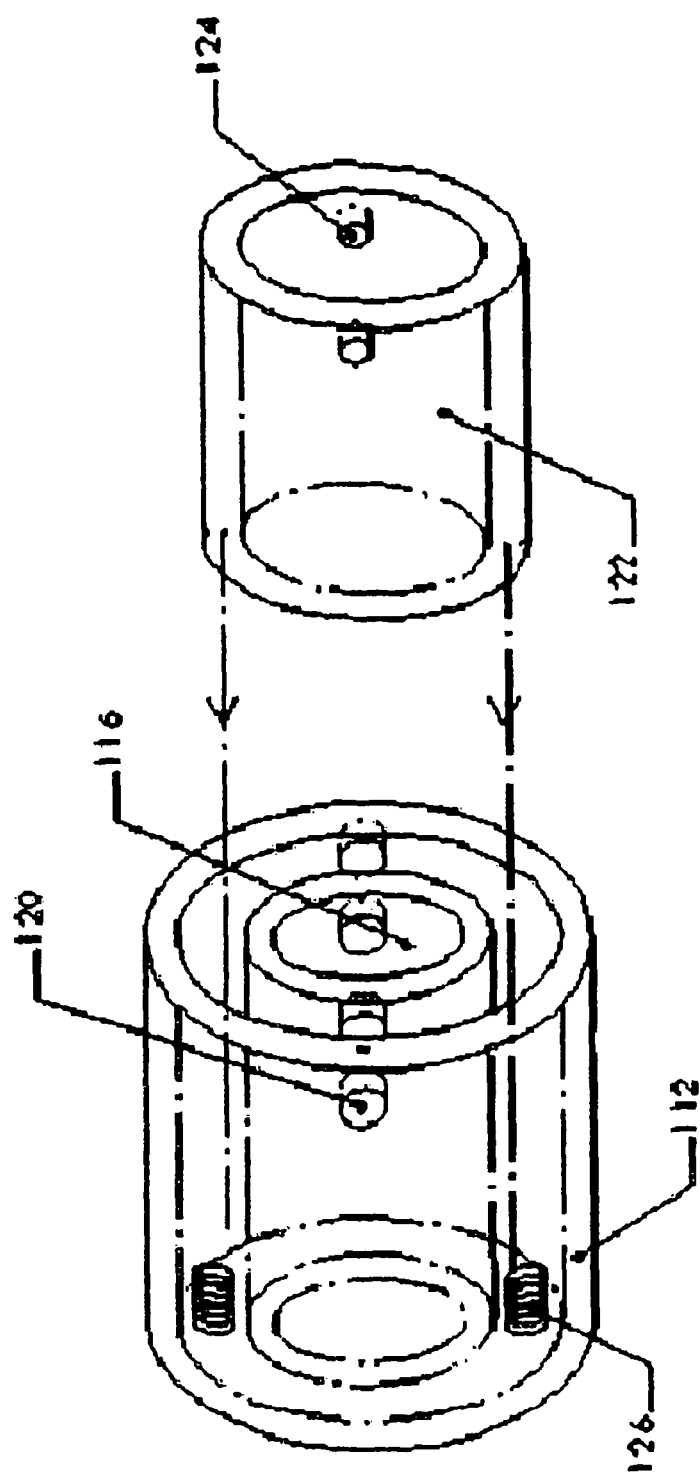

As shown in FIG. 7, the valve closing member 122 may take on any practical configuration, such as a cylinder with the plenum 112. The motion of the closing member 122 to effect opening and closing of valves 118 may be reciprocal as described above or rotary.

Figure 8:
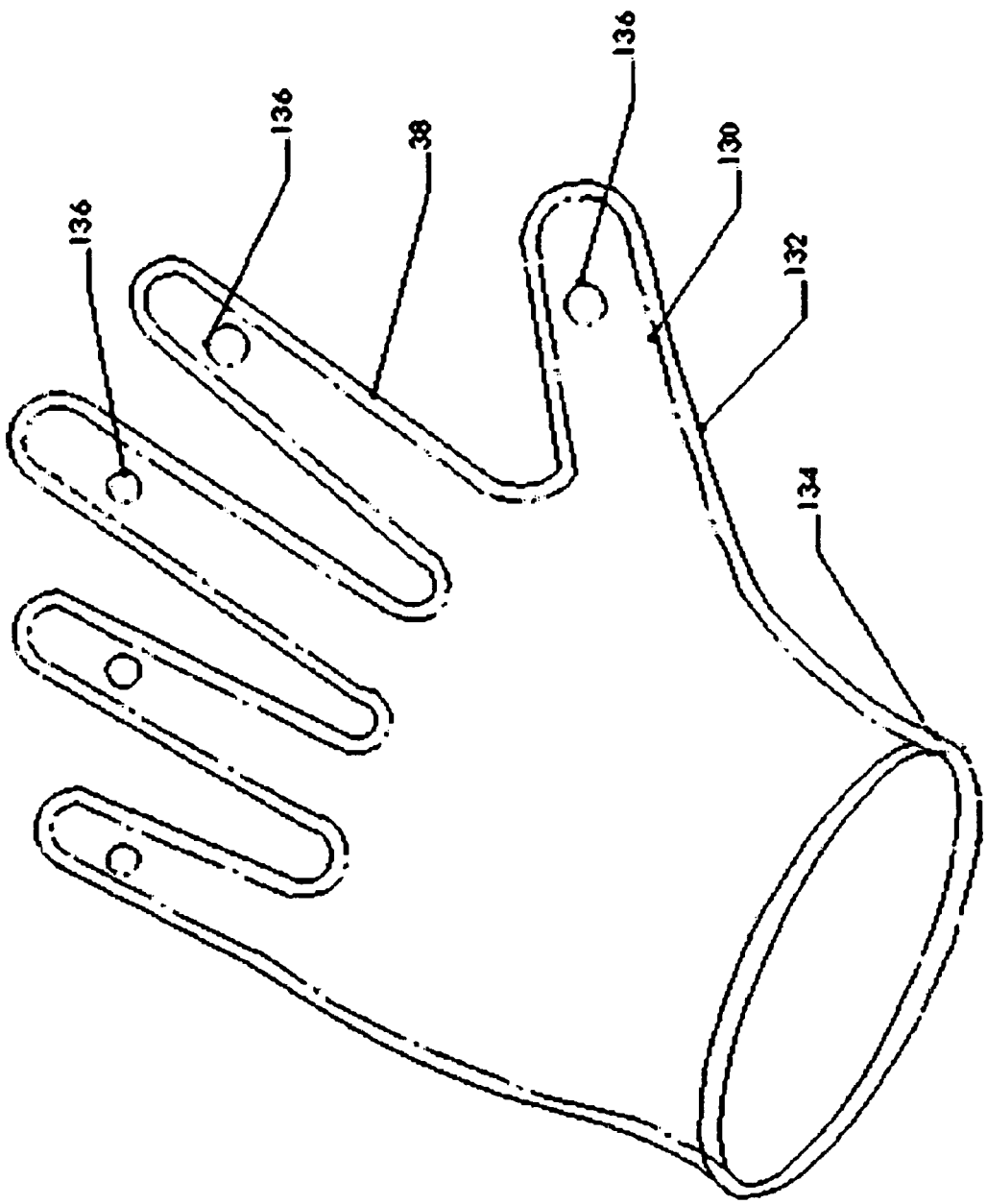
FIG. 8 is a perspective view of a double layered glove used with the isolation chamber shown in FIG. 1.

FIG. 1 shows gloves 38 which allow an operator to manipulate items within the isolation space 16. Gloves 38 are gas impermeable to maintain isolation of the interior space 16 and the barrier space 26 yet flexible to allow dexterous use of the hands when working in the isolation space. Practical materials providing the necessary characteristics for the gloves are known and may comprise nitrile, latex, neoprene, butyl and kevlar compounds. The gloves 38 have an inner layer 130 and an outer layer 132. A barrier space 134 is maintained substantially between the two layers. The inner glove layer 130 is sealed to the sidewall 14 of the inner container 12. This sealing arrangement provides that the barrier space 134 between the gloves is actually in fluid communication with the barrier space 26 between the inner and outer containers 12 and 22. This is advantageous in the event of a leak in the gloves as described below. As shown in FIG. 8, the inner glove layer 130 is attached to the outer glove layer 132 at isolated points 136. Attachment may be effected by fusing the glove layers together and is preferred to prevent the inner glove layer from adhering to the hands of an operator and coming out of the chamber 10 when the hands are removed from the gloves.

Chamber Operation

Figure 1A:
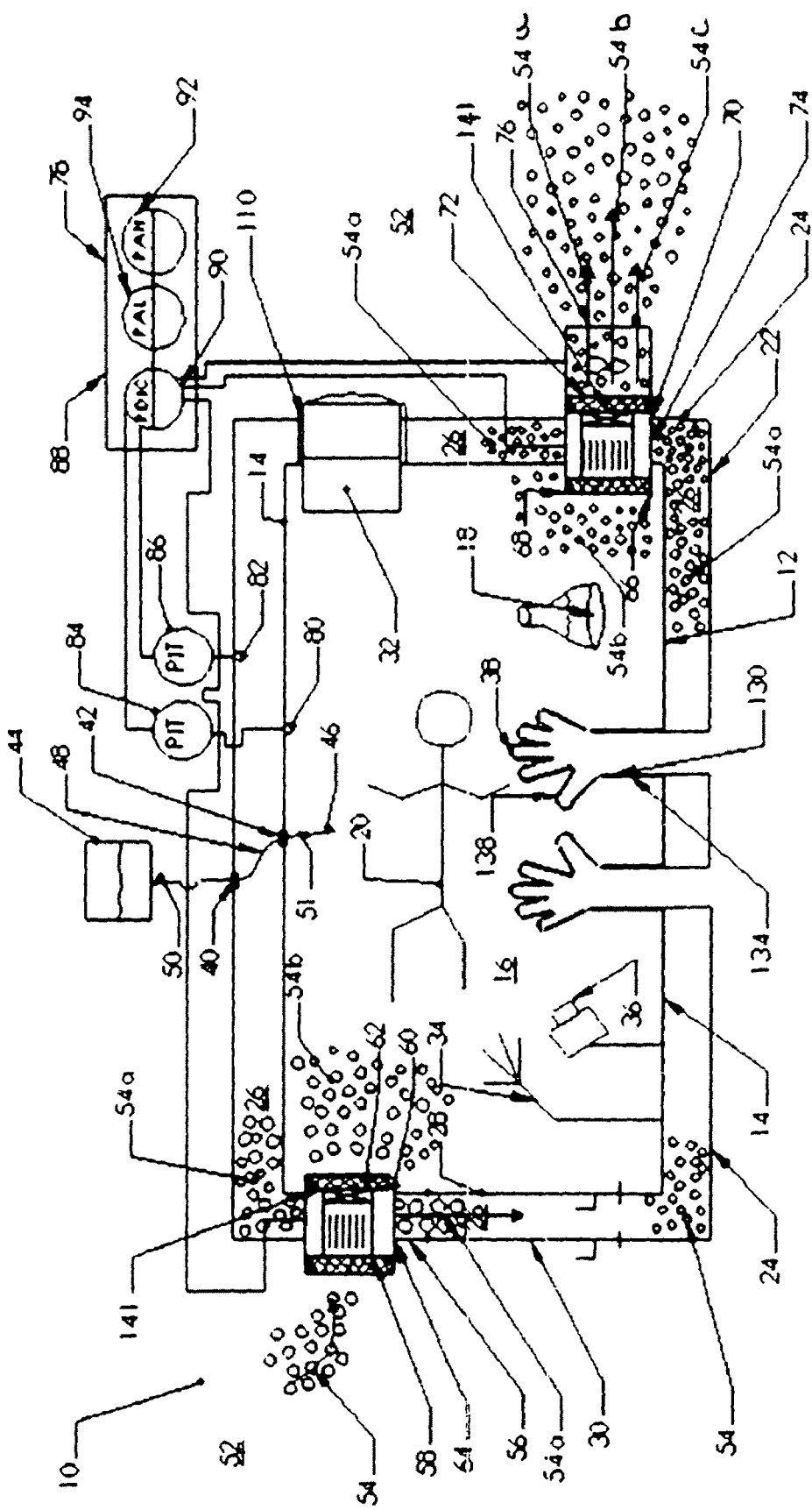

As shown in FIG. 1A, provided with fewer reference characters to simplify the illustration, barrier gas 54 (in this example ambient air) enters the chamber 10 through external intake port 56. The incoming gas is drawn into the chamber by induction blower 76 and filtered by intake filter 58 before passing through the intake 56. Gas 54 then passes through flow splitter 64 which divides the flow, shunting a first portion, 54a, into the barrier space 26, and a second portion, 54b, into the isolation space 16. Flow splitter 64 is under the control of control device 88 which adjusts the flow splitter 64, in conjunction with other components, so that it divides the gas 54 between the barrier space 26 an the isolation space 16 so as to maintain a lower pressure in the isolation space relative to the barrier space. Detailed operation of the flow splitter 64 is provided below.

Gas portion 54a is drawn through the barrier space 26 by the action of induction blower 76. Gas portion 54a generally occupies the barrier space 26 between the inner and outer containers 12 and 22, the glove barrier space 134 between the glove layers 130 and 132, as well as the plenum interior 116 when door 114 is closed. Gas portion 54 b is filtered by intake filter 62 before passing through the internal intake port 60 and into the inner container 12 here it occupies the isolation space 16.

Gas portion 54b is drawn through the isolation space 16 by the induction blower 76 and exits the inner container 12 through internal exhaust port 66. Before exiting, however, the gas portion 54b first passes through a filter 68 which prevents escape of any hazardous materials from the isolation space 16 into the barrier space 26. Gas portion 54a is recombined with gas portion 54b in the flow combiner 74. The combined gas streams 54a and 54b pass through one more filter 72 before being released to the ambient 52.

Pressure sensor 82, located within the barrier space 26, measures the pressure of gas portion 54a within the barrier space 26. Pressure sensor 80, located within the inner container 12, measures the pressure of gas portion 54b occupying the isolation space 16. The pressure information from the barrier space 26 and the isolation space 16 is supplied to the pressure differential indicator and controller 90. the controller 90 uses the pressure information to adjust the operation of the induction blower 76, the flow splitter 64 ad the flow combiner 74 to maintain the gas pressure within the barrier space 26 and the isolation space 16 within the desired limits, as well as to keep the pressure in the isolation space lower than the pressure within the barrier space. This is accomplished by using the low splitter 64 to restrict the volume of gas portion 54b flowing into the inner container 12 so that it is less than the volume which can be drawn out of the inner container 12 through the internal exhaust port 66 by the induction blower 76.

The advantage of maintaining the gas pressure within the isolation space 16 lower than the gas pressure within the barrier space 26 is manifest when there is a leak in the inner container 12. For example, if the sidewall 14 of the inner container 12 is punctured or leaking then barrier gas 54a from the barrier space 26 being under higher relative pressure, will continuously flow into the inner container 12 and leave the chamber 10 only after passing thorough filters 68 and 72. Thus, no hazardous compound will escape from the chamber 10 due to a leak in the inner container 12 or any of its associated components such as the outer glove layer 132. Should the outer glove layer leak, gas from the glove barrier space 134 (actually from the barrier space 26) will pass into the isolation space 16 and out through the exhaust ports 66 and 70 and their associated filters 68 and 72. Gas entering the isolation space 16 and out through the exhaust ports 66 and 70 and their associated filters 68 and 72. Gas entering the isolation space 16 from the barrier space 26 is filtered before entering the barrier space by intake filter 58 and, thus, will be free of pyrogens and other potential contaminants. Thus, in the event of a leak in the inner container 12, the compounds 18 being used in the isolation space 16 will not be contaminated and rendered useless, as would be the case for conventional isolation chambers which, being used under reduced pressure for safety, would draw air in from the ambient and ruin any product or experiment in the chamber. This characteristic makes the chamber 10 according to the invention advantageous to use in the preparation or development of aseptic compounds which would not be compromised by a leak in the inner container 12.

Figure 9:
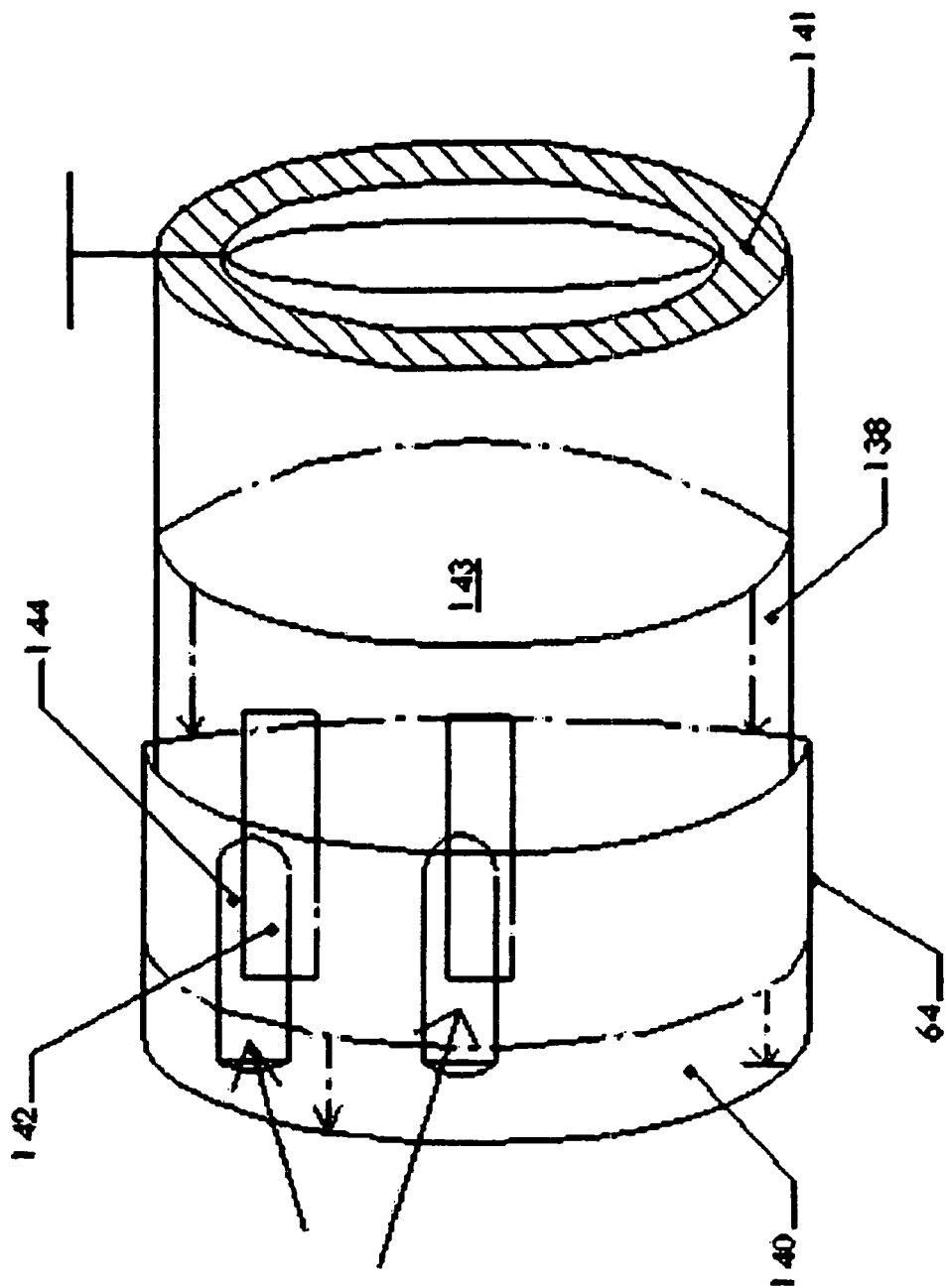
FIG. 9 is a detailed perspective view of a component shown in FIGS. 1 and 1A.

Control of the relative flows and pressures within the chamber 10 is effected by the pressure differential indicator and controller 90 adjusting the operation of the flow splitter 64, the flow combiner 74 and the induction blower 76. The flow splitter 64 and the flow combiner 74 may comprise one or more valves, orifices, baffles or other flow regulating devices which are variably controllable to channel the flow of barrier gas as desired into the barrier space 26 and the isolation space 16. FIG. 9 shows in detail an example of the construction and operation of a flow splitter or flow combiner.

Flow splitter 64 comprises an inner sleeve 138 coaxially located and rotatable within an outer sleeve 140. The sleeves extend between the outer and inner containers 22 and 12 connecting the external intake port 56 with the internal intake port 60. Each sleeve has respective slots 142 and 144 which may be positioned in varying degrees of alignment by relative rotation of the sleeves 138 and 140 to control the relative flow of gas outwardly through the splitter 64 and into the barrier space 26 or the isolation space 16. For example, sleeves 138 and 140 rotated so that the slots 142 and 144 were completely out of alignment and completely closed would channel all of the gas into the isolation space 16. Rotation of the sleeves so that the slots 142 align with slots 144 will allow the greatest volume flow into the barrier space 26. Sleeves 138 and 140 work in conjunction with another flow control device such as valve 141. Also, part of the flow splitter 64, the valve 141 is used to throttle the flow of barrier gas through the bore 143 of the flow splitter 64 and into the isolation space 16 (or outwardly there-from in the case of the combiner 74). By adjusting the opening of the slots 142 and 144 in relation to the opening of valve 141, the flow of barrier gas 54 may be split as required between the barrier space 26 and the isolation space 16. The controller 90 rotates the sleeves 138 and 140 and opens and closes the valve 144 by means of an actuator (not shown) to control the flow of barrier gas in 54 in response to the pressure information from the pressure sensors 80 and 82 and according to an algorithm, preferably encoded in software resident in the control system 88, preferably a computer.

Figure 10:
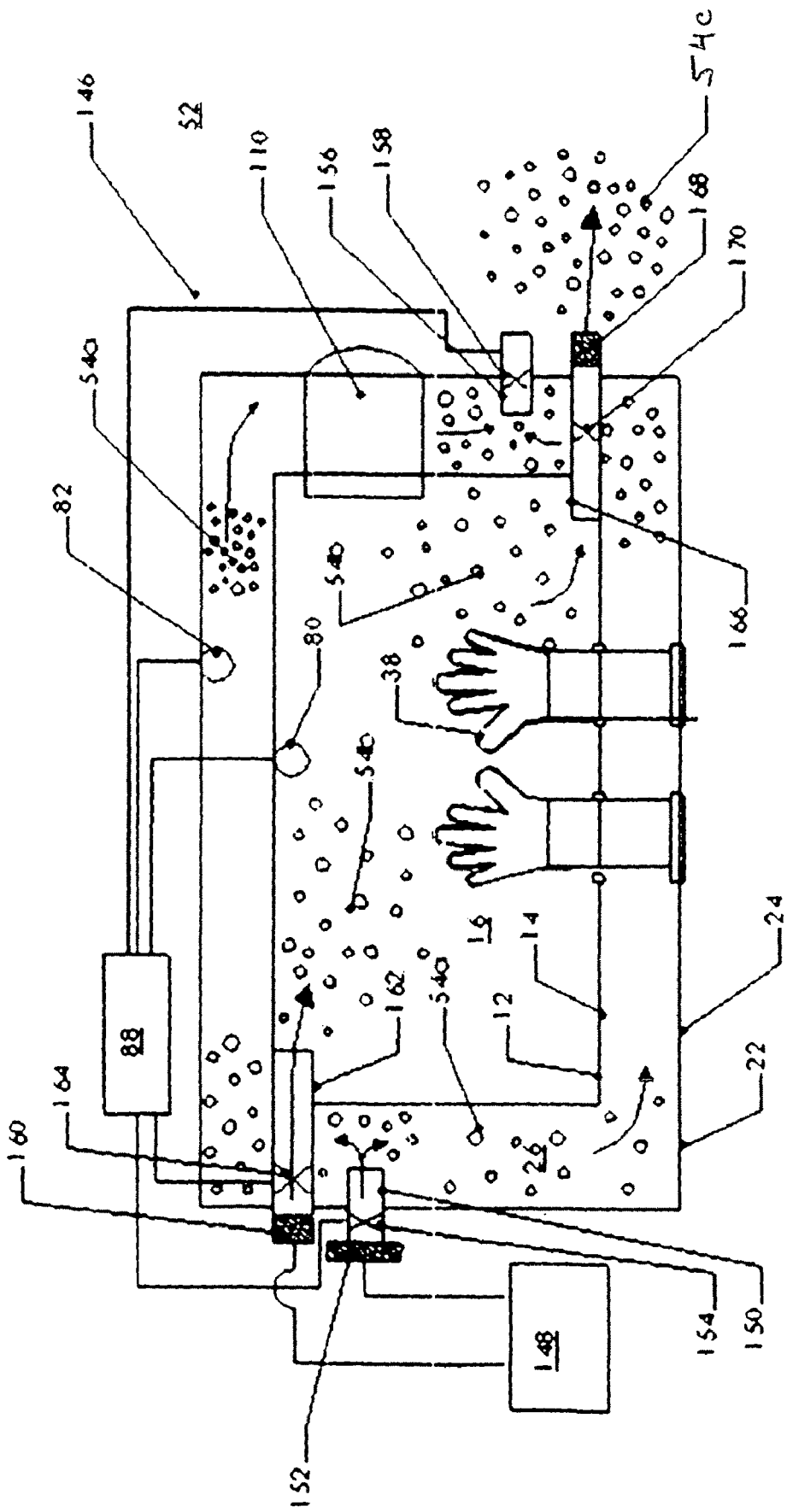
FIG. 10 is a schematic view of an alternate embodiment of an isolation chamber according to the invention.

An alternate embodiment of the chamber 146 according to the invention is shown in FIG. 10. Chamber 146 comprises an inner container 12 having sidewalls 14, the inner container surrounding and defining an isolation space 16. Chamber 146 also has an outer container 22 having sidewalls 24 surrounding the inner container 12 and defining a barrier space 26 between the inner and outer containers. Barrier gas 54a at elevated pressure as compared with the ambient 52 is introduced into the barrier space 26 form a gas source 148, which could be a compressor or a pressurized reservoir, through an intake port 150 located in sidewall 24 and providing fluid communication to the barrier space 26. Before entering the barrier space 26 the barrier gas 54a passes through a filter 152, ensuring no contaminants are present in the barrier space 26. A servo actuated valve 154, under the control of a control system 88 regulates the flow of barrier gas 5a into the barrier space. Escape of barrier gas 54a from the barrier space to the ambient 52 is controlled by exhaust port 156 located in sidewall 24, the exhaust port having another servo valve 158 under the control system 88. Pressure sensor 82 within the barrier space 26 feeds information to the control system 88, which adjusts the valves 154 and 158 accordingly to maintain the desired pressure within the barrier space.

Similarly, pressurized gas 54b is supplied to the isolation space 16 from a gas source such as 148 or another source. The gas 54b passes through a filter 160 before entering the isolation space 16 through an intake port 162 which traverses the barrier space 26. A valve 164 under control of the control system 88 regulates the flow of gas 54b into the isolation space. The gas 54b is permitted to escape from the isolation space 16 to the ambient 52 through an exhaust port 166 which traverses the barrier space 26 to provide fluid communication between the inner container 12 and the ambient 52. Gas 54b passes through a filter 168 associated with the exhaust port 166 and its flow from the isolation space 16 to the ambient 52 is regulated by a valve 170 located in the exhaust port and under the control of a control system 88. Pressure sensor 80 within isolation space 16 feeds the control system 88 with signals indicative of the pressure of gas 54b within the isolation space 16 allowing the control system to regulate the flow of gas 54a and 54b through the chamber so as to maintain the relative pressures of the gases as desired, preferably with the barrier space pressure higher than ambient and the isolation space pressure below that of the barrier space to achieve the advantages of operation as described above. The chamber 146 also may have a transfer port 32 and gloves 38, as well as other components described previously.

Isolation chambers having dynamic barriers according to the invention provide an enhance degree of safety of operation over conventional isolation chambers and allow aseptic materials to be handled or patients vulnerable to infection to be treated without fear that a leak in the system will compromise the cleanliness of the isolation space and threaten the patient with infection or aseptic compounds with contamination. Chambers according to the invention may be constructed from any practical material and may be made portable for ease of transport, for example, to and from a medical emergency or disaster site, may be fixed installations such as for use in a laboratory, and may be of any practical size, from a desktop model to a room sized construction.

Mechanical Component Transfer System

Figure 11:
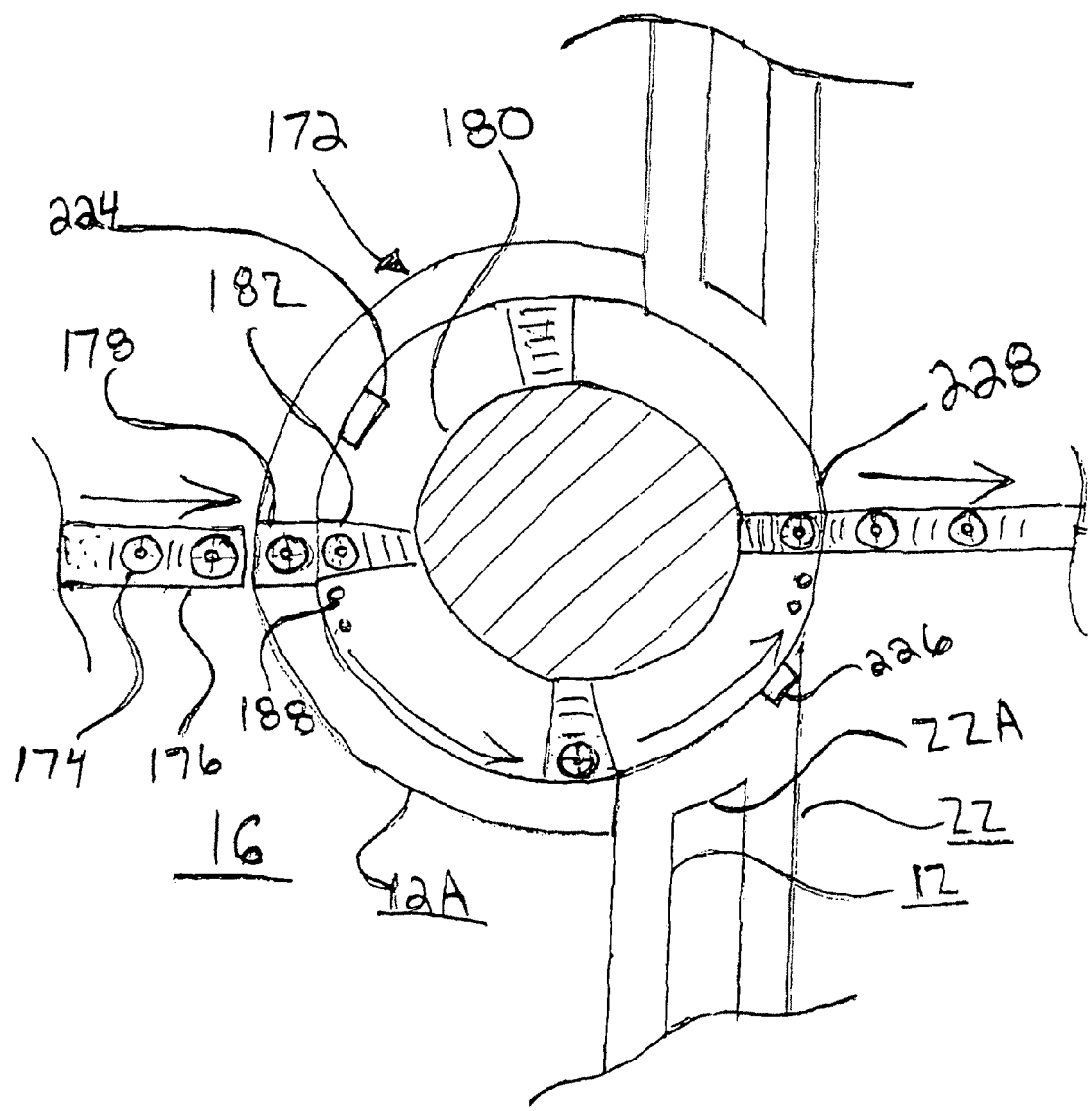
FIG. 11 is a top view of a vial transfer system in accordance with the present invention which may be used with an isolation chamber or other containment system.
Figure 11A:
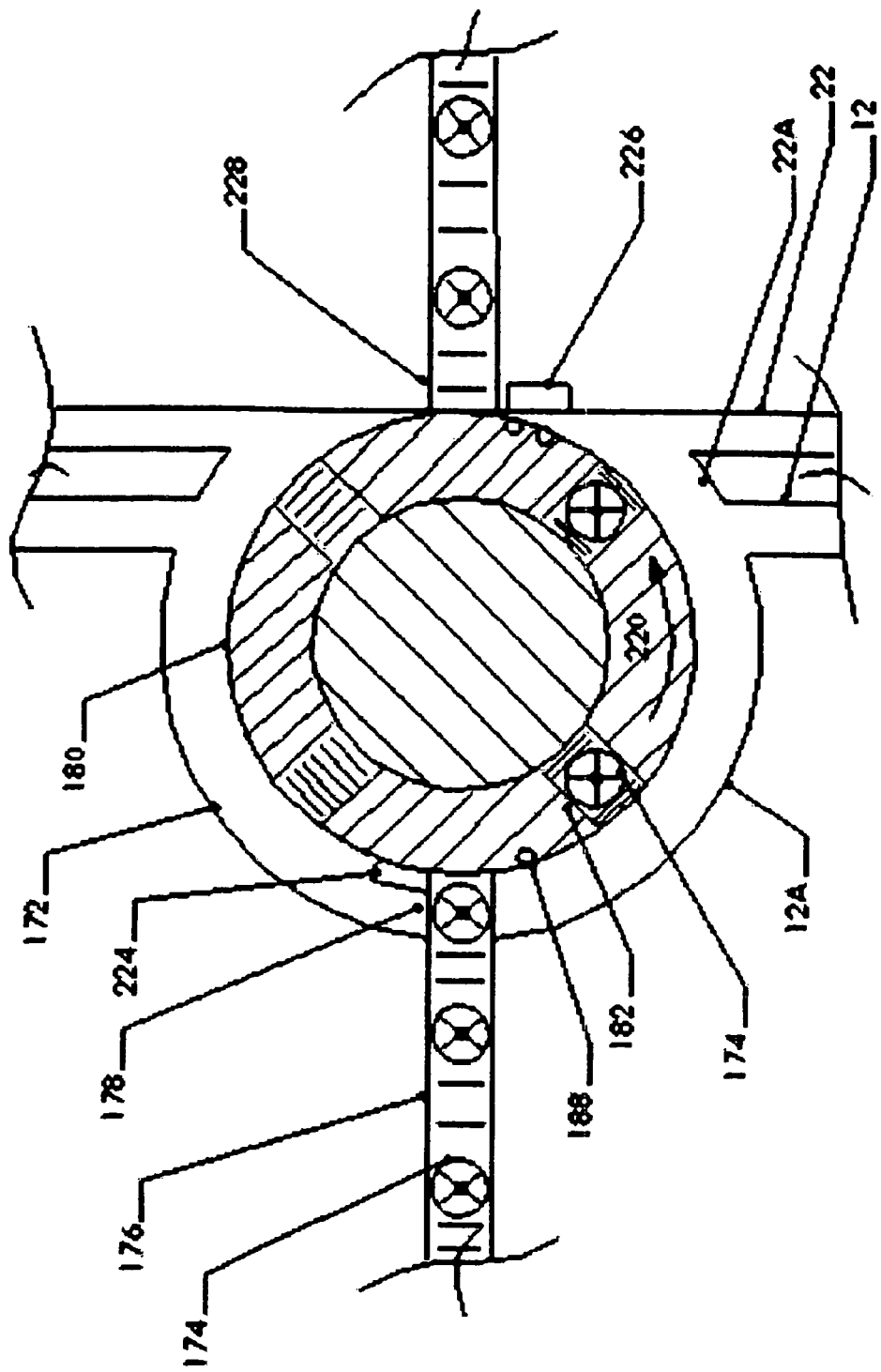
FIG. 11A is a top view of the vial transfer system shown in FIG. 11 showing the general operation of the turntable system.

Referring now to FIGS. 11 and 11A, a component transfer system in accordance with the present invention is indicated at 172. The Dynamic Barrier Isolation Chamber or other traditional or containment systems may be equipped with the mechanical transfer system 172 in lieu of, or in addition to, any transfer port designed to provide egress from or ingress to said chamber. Vials are illustrated herein; however, one skilled in the art, after a thorough reading of the present disclosure would be able to modify the present invention to accommodate any sized objects, including large equipment, parts, components, humans or animals.

The mechanical transfer system 172 is disclosed herein in its preferred embodiment as a device for transferring vials form one position within a contained space 16 to another position within or outside of the initial or an adjacent contained barrier space. The mechanical transfer system 172 will allow large equipment, humans or animals to pass between compartments within a containment system or to pass between compartments within the system to and from the ambient or other area outside of the system. It may also transfer tablets or other components in a similar way. In this embodiment, vials 174 used for the containment of parental (pyrogen free injectable) potent compounds (high concentration of pharmaceutical active ingredient) are conveyed mechanically, through a vial transfer chute 176 to a vial transfer chamber 178 by indexing, continuous feed and or other conventional method of moving vials currently know in the art.

The mechanical transfer system 172 includes a vial transfer chamber 178 and a rotating assembly 180. The rotating assembly 180 acts like a turntable or a "Lazy Susan" for moving the vials in a circular motion. The vial transfer chamber 178 is a compartment within the rotating assembly 180 of the mechanical transfer system 172.

The vial transfer chamber 178 is an opening having of four enclosed sides forming an entrance through an inner barrier wall 12A between the barrier space 16 and the rotating assembly 180 of the Mechanical Transfer System 172. Subsequent positioning of vials 174 into the vial transfer chamber 178 by continuous or intermittent forces serves to displace the vial 174 from the vial transfer chamber 178 by moving it into the transfer compartment 182 of the rotating assembly 180.

The vial transfer compartment 182 is generally cubical in shape for this embodiment, but may be cylindrical or other functional shape, and is made of two parts in this embodiment; the first of which is the vial transfer space 184 and the second part is the vial ejector mechanism 186.

The vial transfer space 184 is made of a perforated floor and ceiling 188 and 188A with pluggable or other wise controlled openings to permit the flow of fluid vertically, in this embodiment while horizontal flow would be another option, through the vial holding space without being large enough to permit vial instability or vial egress. The fluid may be liquid, gas or vapor phase and it may be introduced in numerous combinations and flow patterns and rates such as top to bottom, pulsing or continuous as shown in this embodiment 190. The fluid flow through this portion of the Dynamic Barrier Isolator system is controlled by the PLC based control system 78. The recessed or rear of the vial transfer compartment 182, or that area farthest from the opening contains the vial ejector mechanism 186.

Figure 12:
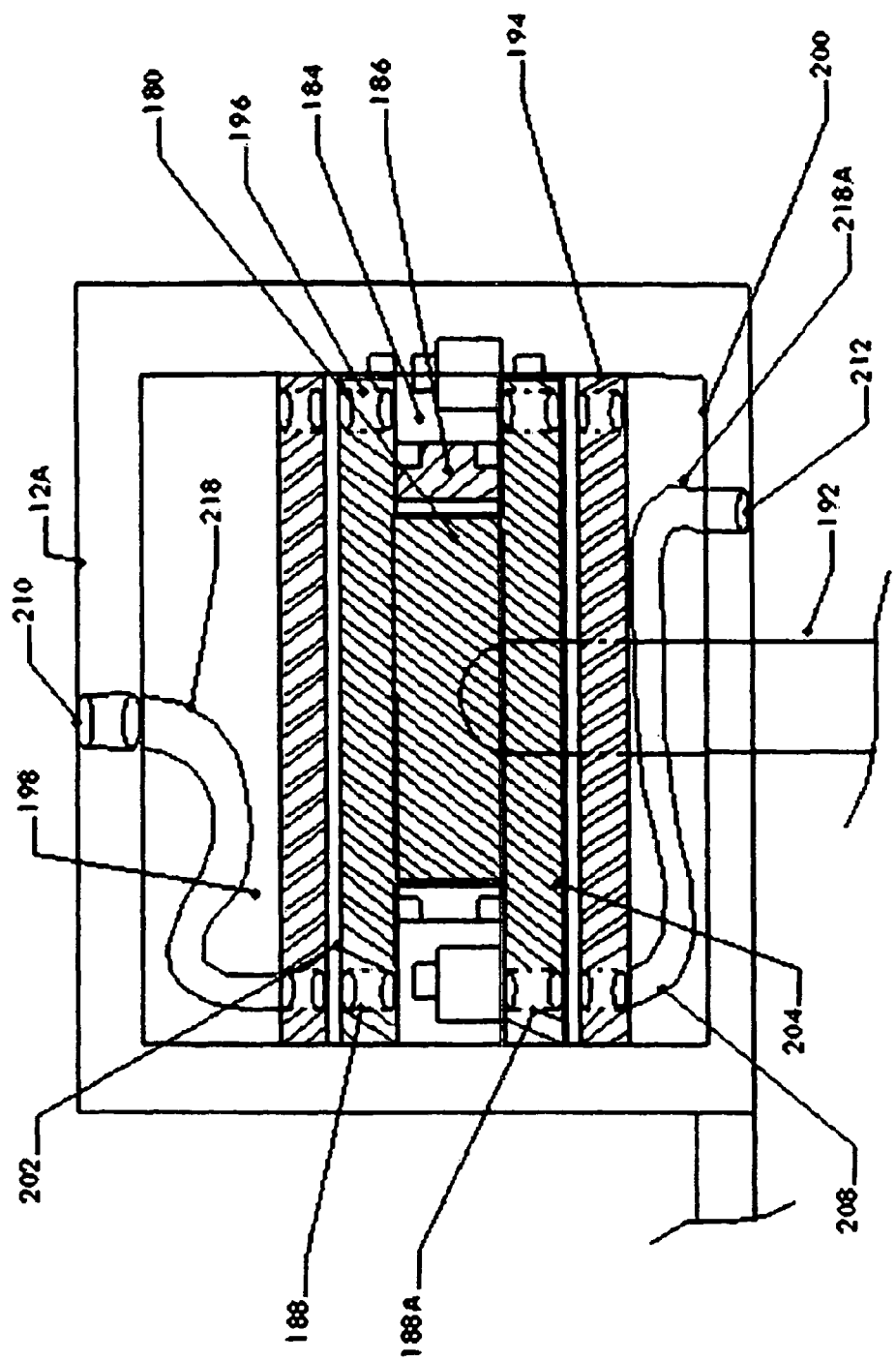
FIG. 12 is a cross-sectional side view of the vial transfer system shown in FIG. 11.

Referring now to FIG. 12, the rotating assembly 180 containing the vial transfer compartment 182 may be indexing, continuous or manually actuated. The preferred embodiment is that the rotating assembly 180 be powered by a trough the barrier, sanitary, cleanable, magnetic, coupling drive assembly 192, of the basic design in existing service in sanitary liquid systems such as mixing tanks and controlled by a PLC bases control system 78. Magnetic coupled mixers and pumps are devices generally known and comprise, for example a variable frequency drive, gear boxes, and balanced liquid cooled shafts and impellers all designed to operate within a liquid medium, utilizing the liquid as a coolant, spacer and lubricant, for the sole purpose of imparting motive force to the liquid medium. These magnetic drive impeller systems are especially inadequate when called upon to operate in the absence of a liquid coolant and lubricant. These magnetic drive systems do not impart enough continuous, guaranteed torque to be of a traditional commercial value in applications apart from liquid movements such as for the traditional driver for gears. They are particularly will suited for any application where the forces acting upon the drive, drive coupler and the hub such as an impeller or gear are not uniformly distributed such as to minimize angular torque between the drive coupler and the driven component to prevent galling of the coupler shaft or driven hub.

This embodiment uses magnetic couplers in a non-traditional, unique and novel application outside of the normally required liquid coolant and lubricant environment. The rotating assembly 180 s in its entirety the hub component of a magnetic coupled drive system. The hub and the sanitary enclosed magnetic coupler which drives the hub, one or both, are protected from friction induced heat build-up, galling, nicking and wobble by the insertion of a Teflon, or other specific process suitable material, diaphragm between the magnetic coupling and the hub. This diaphragm may be preformed, form fitting or moldable in place into either the hub receiver or onto the magnetic coupling driver shaft. It may be cleanable and reusable or a single use consumable as in this embodiment. An alternative embodiment of the diaphragm is in the form of an insoluble or soluble material such as, but not limited to soap, glycerol based materials, Teflon polymer mixtures and other sealing, bearing, or lubricating materials generally known and suitable for use in cGMP environments or other wise found to be suitable for this invention.

The rotating assembly 180 is enclosed on all sides by a barrier wall or plurality of barrier walls 194 and 196 with specific openings where called for elsewhere in this document or as required by a specific chemical or pharmaceutical or other process. The barrier wall 196 and the top of the inner containment wall 12A enclose a plenum 198. The barrier wall 194 and the bottom of the inner containment wall 12A enclose a plenum 200. The spaces 202 and 204 between the rotating assembly 180 and the barrier walls 194 and 196 is adjustable by manufacturing design to meet the needs of the process.

Barrier walls 12A, 194, 196 an the rotating assembly 180 contain from top to bottom upper and lower precisely located apertures 210, 206, 188, 188A, 212 permitting, under predetermined process conditions and control by the controller 78, communication between fluids in all contained spaces while maintaining barrier integrity during normal operation and in the event of a system or component failure, failing in a contained and safe mode preventing communication of contaminants.

Figure 13:
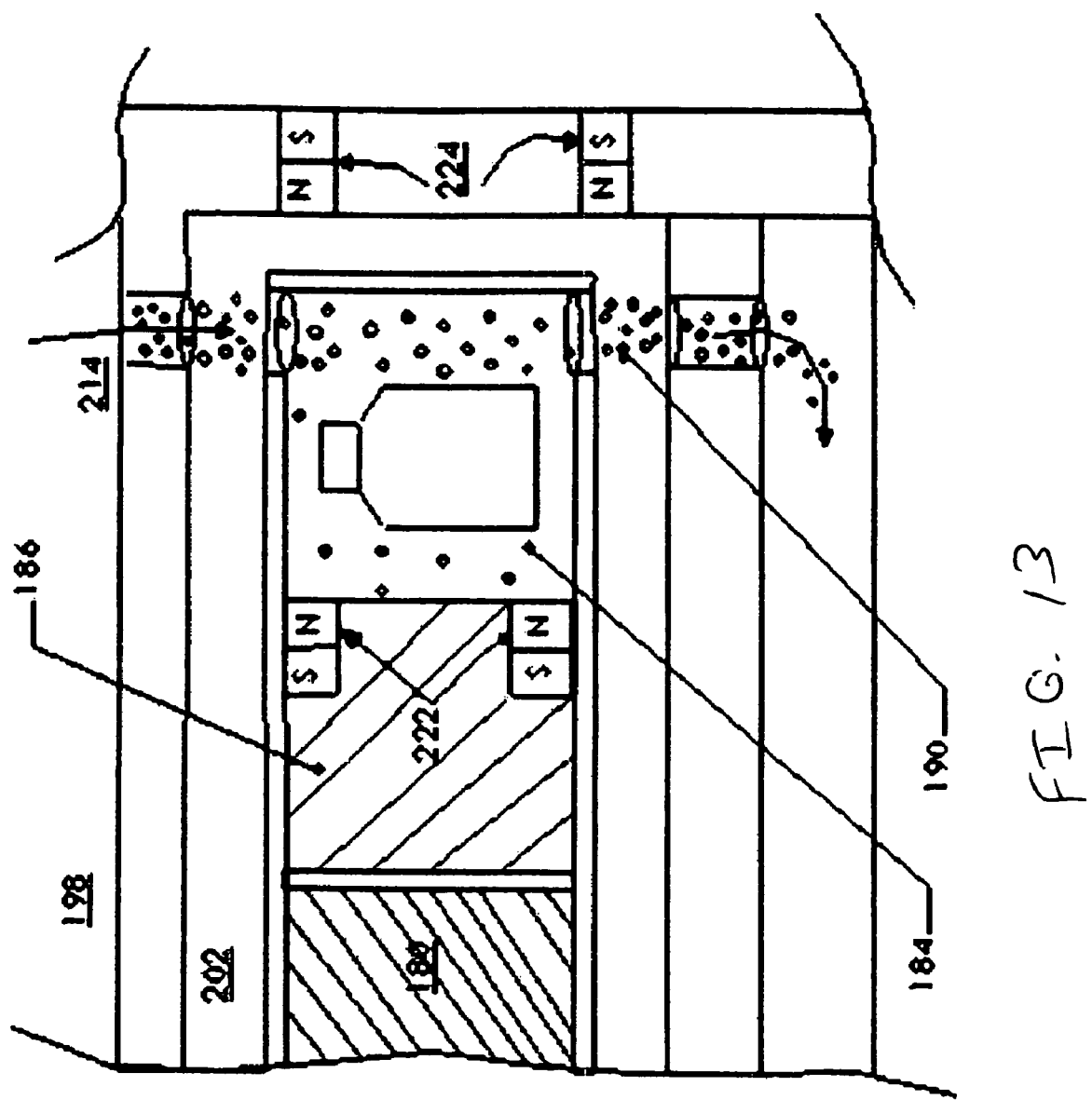
FIG. 13 is an enlarged partial view of the vial transfer system shown in FIG. 12.
Figure 13A:
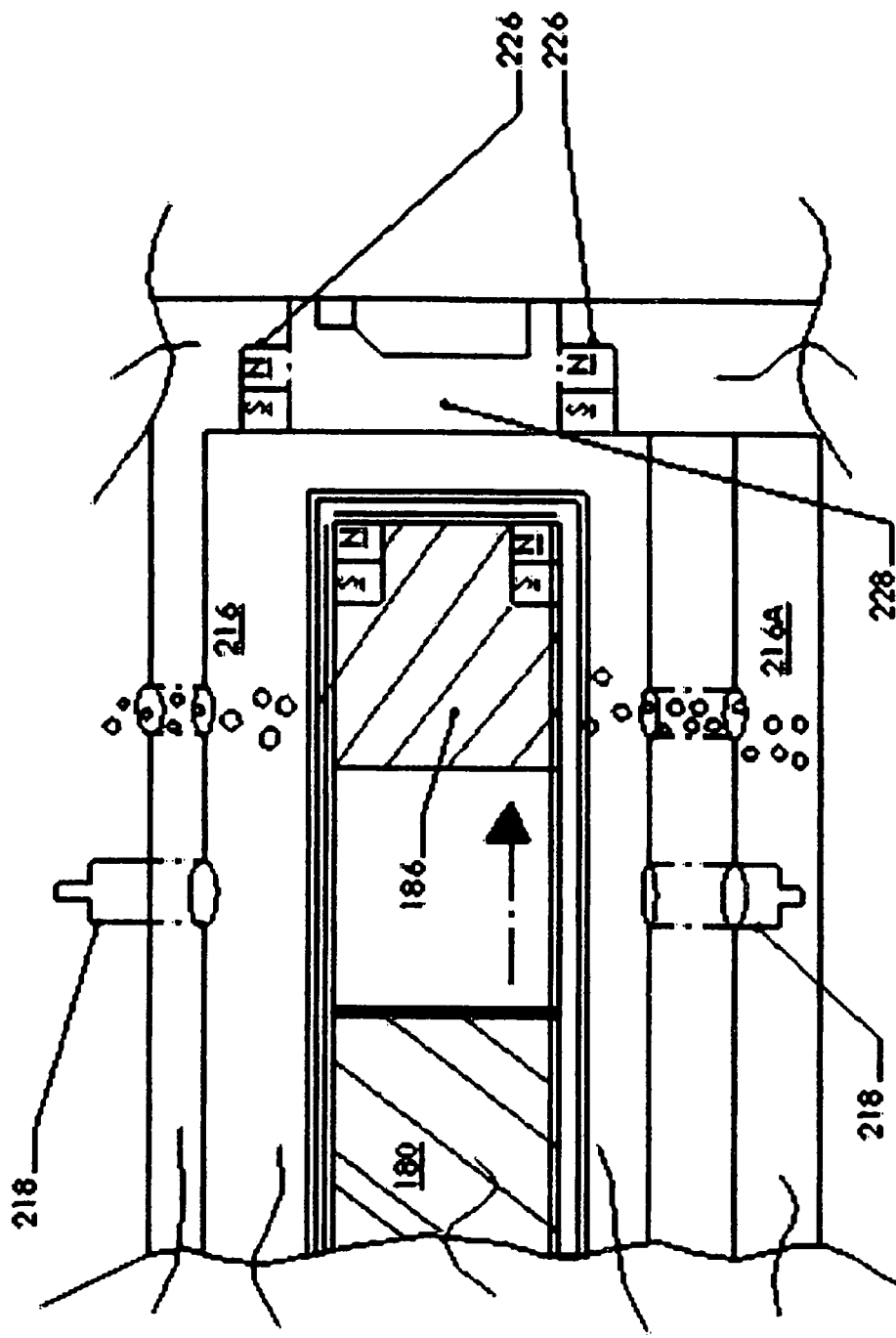
FIG. 13A is a close-up view of a vial ejector system shown in FIG. 13.

In this embodiment of the invention, the described communication between fluids during normal operation is intermittent as shown in FIGS. 13 and 13A by fluid flow 214 and 216 respectively.

In this embodiment, the intermittent nature of the fluid flow is designed to permit for a pulsing effect of the fluids passing through the vial holding space 184 and across the vial 174. This intermittent zoned pulsing effect may be enhanced by alternately introducing different fluids such as but not limited to, air, nitrogen, specialty gases, water, cleaving solvent, or sterilizing chemicals. The effect between pulsing and continued flow may be adjusted by increasing the size of or number or apertures 206, 208 188, and 188A in the appropriate barriers or by the command of a control system 78. The succinct delivery or recovery of any fluid may be directed for a utility station or manifold via standard, generally available valve mechanism, through rigid or flexible tubing 218 and 218A. Additional ports similar to 210 and 212 may be added as required for the collection of real or potential fugitive gases, vapors or liquids, with or without contaminants. This embodiment of the invention depicts the flows within the Dynamic Barrier Isolation Chamber, including those flows through the Mechanical Transfer System 172. The source of the flows may be from within the barrier or from on or plurality of sources exterior to the isolation chamber.

In this embodiment, the vial enters the vial transfer chamber 178, with the positioning of the rotating assembly 180 such that the aperture misalignment between apertures 188, 188A, 206 and 208 does not permit the communication of fluids between the barrier space 16 or plenum 198 and 200 as depicted in FIG. 11. As the vial transfer compartment 182 rotates 220 through its 360 degree cycle shown in FIG. 11A, the vial holding space 184 containing the first vial is first enclosed by the walls of the transfer compartment 182 and the barrier wall 12A which serves to isolate the vial from fluid communication with the barrier space 16. This isolation of vial transfer chambers from the isolator containment space 16 will remain in effect until the next empty vial holding space 184 rotates into position to receive the next vial in the transfer chamber 178.

As the transfer compartment 182 rotates, its apertures 188 and 188A come into alignment with apertures 206 and 208 permitting the communication of fluids between the spaces 184, 198, 200, 202, 204, and the apertures 210 and 212. Further rotation misaligns the apertures disrupting the communication between fluids in the spaces 184, 198, 200, 202, 204, and the apertures 210 and 212. The number of apertures and fluid communication events is governed by the process requirements.

At the end of the rotation cycle, which in its current embodiment has a rotation through less than 360 degrees and a process defined number of fluid communication events, the transfer compartment 182 rotates into position to eject the vial from the mechanical transfer system 172 as illustrated in FIGS. 13 and 13A.

The vial ejector mechanism 186 in this embodiment has a shaped cubic form designed to move freely in a radial direction within the transfer compartment 182 without exiting the compartment during loading or ejection of vials. It is secured in place during most of the rotation cycle by the repulsion forces of magnets 222 and 224. Magnets 222, or plurality there of, are embedded or otherwise attached to the vial ejector mechanism 186. Magnets or plurality thereof, 224 are embedded or attached in either the barrier wall 12A, 194 or 196 or an equivalent location determined by the process requirements based upon the physical characteristics of the specific components. As the ejector mechanism 186 approaches the vial exit port 228, it approaches magnets 226 or plurality thereof. Magnets 226 are oriented opposite to the magnets 224 providing for an attractive force between magnets 222 and 226. This attractive force, working together with the naturally occurring centrifugal forces present in any rotating object serve as the motive force to eject the vial from the transfer compartment 182 and from the mechanical transfer system 172 to a receiving system, not shown.

Mechanical Equipment Transfer Station

Figure 14:
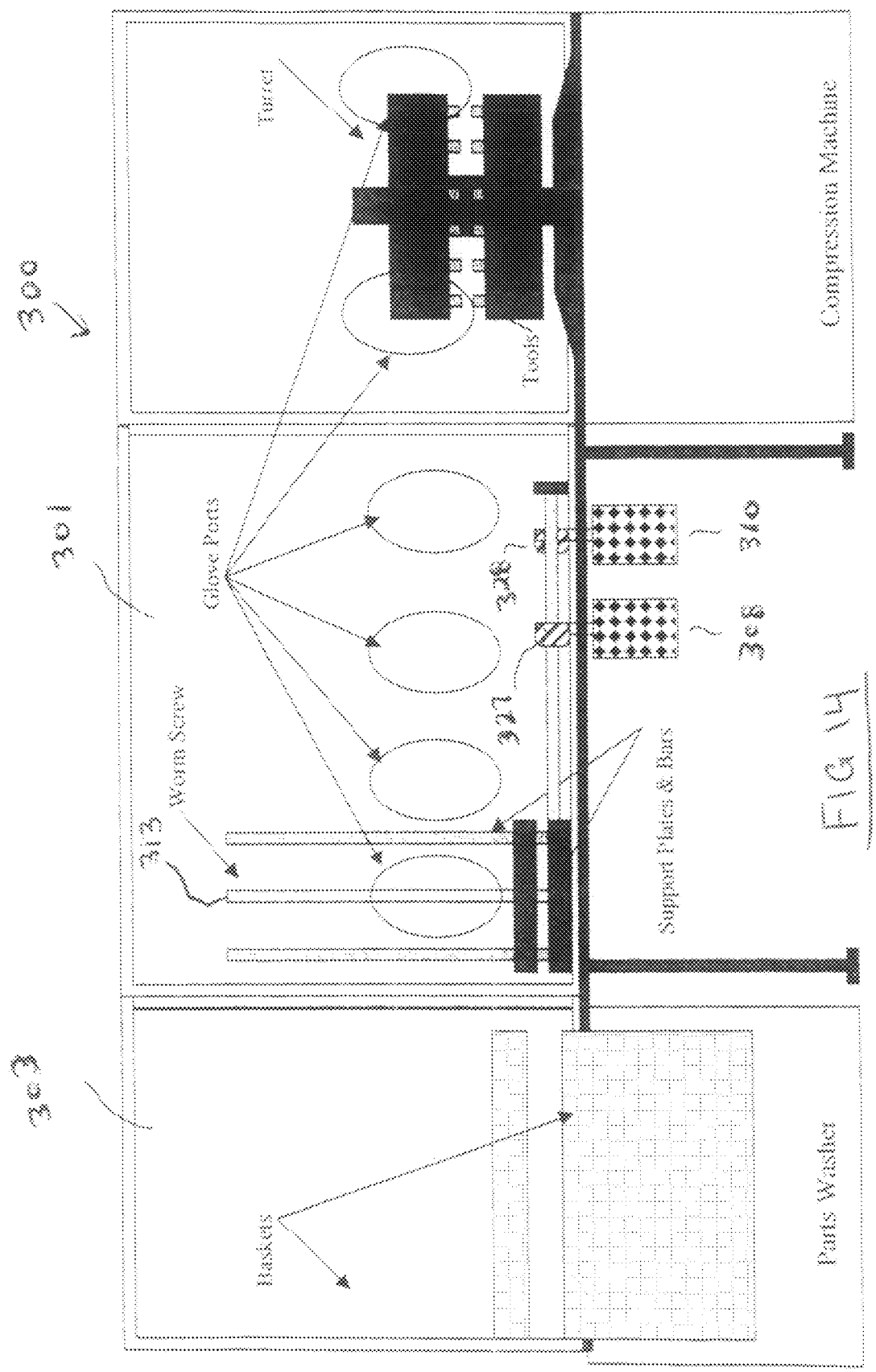
FIG. 14 is a schematic side view of an equipment manipulation chamber utilizing a magnetic drive assemble in accordance with the present invention.

Referring now to FIG. 14, an equipment transfer station is generally indicated at 300. The mechanical equipment transfer station 300 was designed for use with the dynamic barrier isolation system in environments where the traditional methods of equipment operation, handling or cleaning are impeded by the presence of potent or hazardous compounds. The Dynamic Barrier Isolation Chamber is configured such that it may be joined with other equipment including, but not limited to, compression machines, parts or glass washers or vial filling lines also protected by a dynamic barrier isolator system. This embodiment of the invention is designed for use in hazardous, clean, aseptic, isolation or containment environments such as areas with electrical classification of Class 1 Division 1 and or Division 2. Hazardous chemical environments, hazardous biological areas, potent drug areas, cytotoxic drug areas. This invention permits this Mechanical Contained Equipment Transfer Station to be used with traditional barrier isolators currently available on the market without requiring the use of the dynamic barrier system. It also permits the retrofitting of existing barrier isolator containment system.

This Mechanical Contained Equipment Transfer Station 301 in its preferred embodiment is depicted in the schematic drawing FIG. 14 as a universal compression machine component manipulator and transfer device. This embodiment shows the Mechanical Contained Equipment Transfer Station 301 joined with a compression machine (tabled press) 302 used in the manufacturing or compression of potent compounds used in solid oral dosage forms. The system is then linked to a parts washer 303 for this embodiment.

Figure 15:
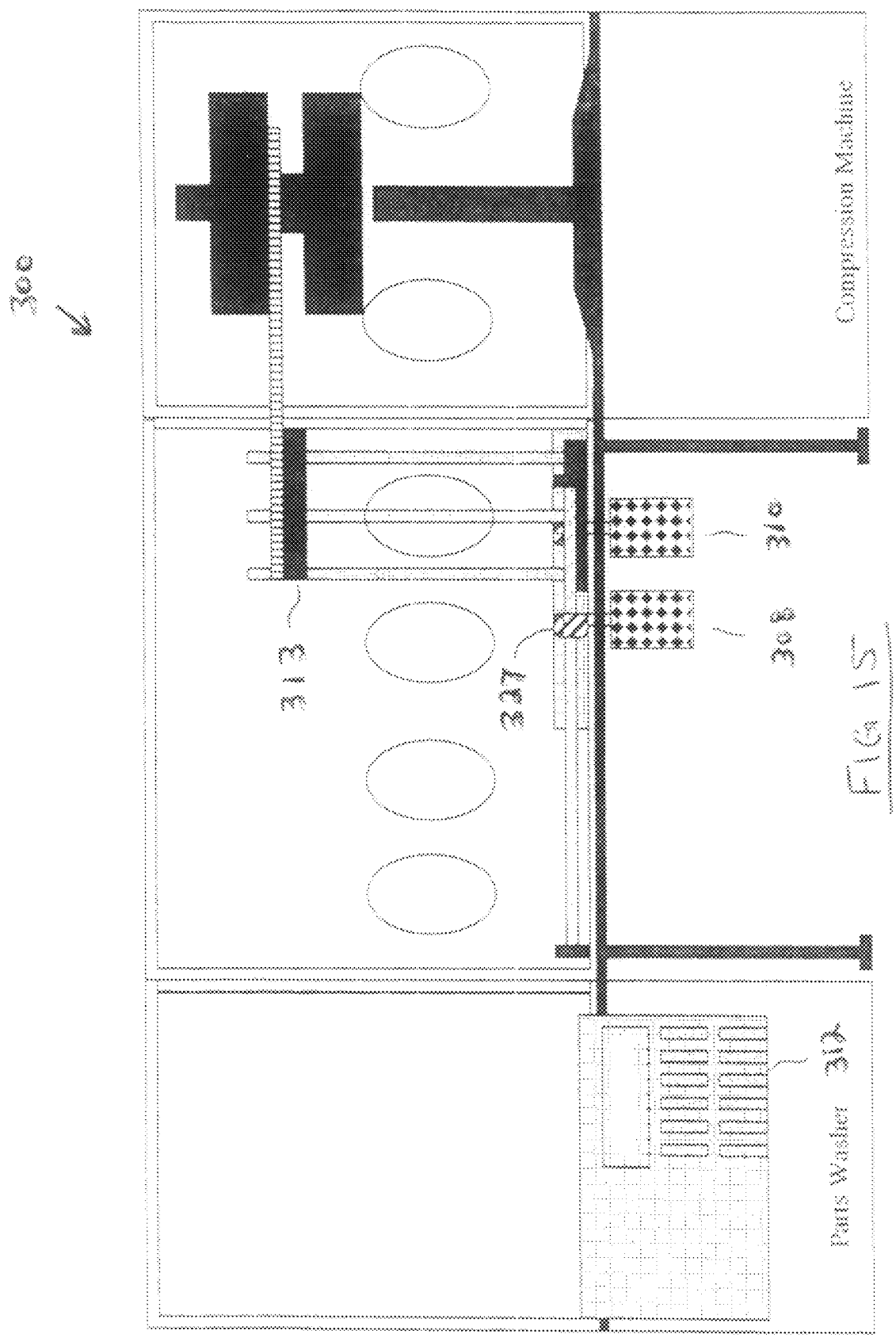
FIG. 15 is a side view of the equipment manipulation chamber shown in FIG. 14 showing the equipment form the compression machine in partially disassembled.
Figure 16:
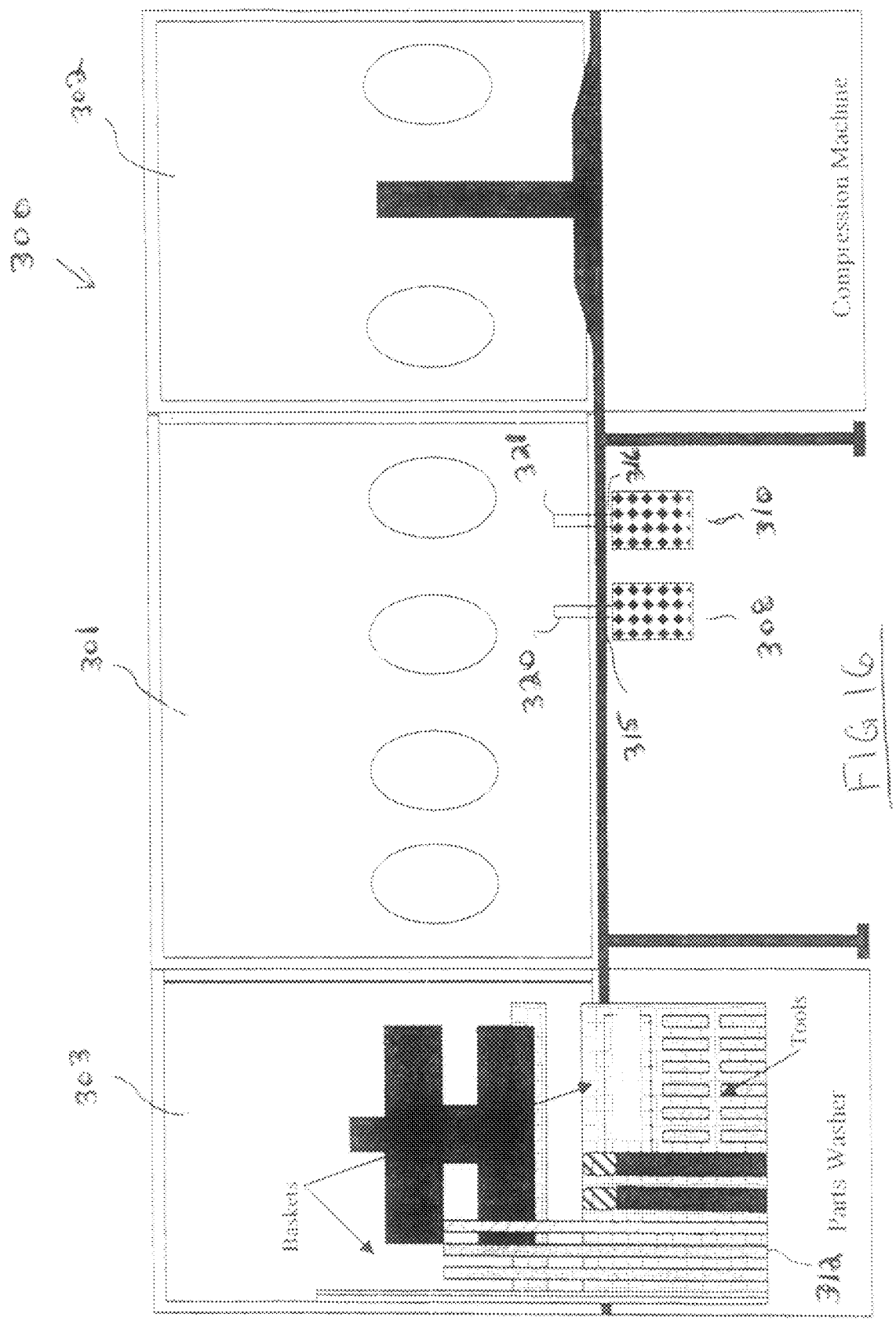
FIG. 16 is a side view of the equipment manipulation chamber shown in FIGS. 14 and 15 showing the equipment from the compression machine in fully disassembled.

Solid dose compression machines (tablet presses or capsule fillers) which are not currently of a design that may be cleaned in place (CIP). The wash in place (WIP) systems currently employed clean most of the potent materials from the press components. Operators must still manually disassemble the compression machines in order to ensure that all parts are cleaned to cGMP/FDA/OSHA/EU compliance. As illustrated in FIGS. 15 and 16, the disassembled parts 312 are then transported to a parts washer 303 for a thorough cleaning, chemical deactivation and later sterilization if required. "The contained equipment transfer station 300 in this embodiment is a containment system (glove box type) designed to transfer all of the disassembled equipment components form a contaminated area (typically form within another isolator) while never exposing the operator to the hazardous or potent compound. The immediate obstacle to overcome in transferring such components is the size and weight of traditional compression turrets. While some compression machine manufacturers currently use some lifting device to manipulate their respective components, no device currently exist that will manipulate a variety of turrets manufactured by a variety of compression machine manufacturers until the invention of this mechanical contained equipment transfer station 300.

The transfer station must be capable of lifting objects that are significantly heavier than the vials illustrated in FIG. 11. As shown in FIGS. 14, 15 and 16, magnetic drive mixers 308, 310 are located outside of the chamber but provide the motive force to move the lift 313 in the transfer station 300.

Referring to FIG. 16, the magnetic drives 308, 310 have a shafts 315, 316 respectively that are inserted into inward projections 320, 321. The inward projections are a part f the floor of the transfer station 300.

Referring again to FIG. 14, a gear wheel 327, 328 is associated with each magnetic drive. The gear wheels have a circular portion with gear teeth on the perimeter of the circular portion, and an elongate portion extending axially from the center of the circular portion. The elongated portion 330, 331 is designed to form fit relatively snugly over their respective shaft. In an alternative embodiment, the gear wheels may be cylindrical in shape and have the requisite extension to fit over the inward projections. The gear wheels are designed to fit complementary gears of the worm crew, lift 313 or other machinery utilized within the transfer station 301.

The magnetic drive 308 turns shaft 315. When shaft 315 rotates, the gear wheel 320 is magnetically coupled to the shaft through the inward projection and turns substantially in unison with said shaft. Any machinery within the transfer station may derive its motive energy from the rotating worm gear(s).

An important feature of this invention is a diaphragm 333 designed to snugly fit over said inward projection. The diaphragm is specially treated with a lubricant for reducing friction between the elongate portion of the gear wheel and said inward projection.

Although this invention has been described and illustrated by reference to specific embodiments, it will be apparent to those skilled in the art that various changes and modifications may be made which clearly fall within the scope of this invention. The present invention is intended to be protected broadly within the spirit and scope of the appended claims.

I claim:

1. An isolation device for proactively simultaneously isolating high value potent aseptic parenteral substances from the ambient and protecting the environment from fugitive potent materials using an elevated pressure fluid curtain in gas or liquid phase, in the form of a dynamic fluid barrier, channeled within a multi-walled isolation device, where the dynamic fluid barrier serves as a fluid plug immediately adjacent to any solid isolator materials for the purpose of plugging any breach in any adjacent solid isolator material using a fluid, said multi-walled device designed to channel the dynamic fluid barrier comprising: a. first container surrounding and defining an isolation space for holding said substances; a second container surrounding the said first container and spaced apart from said first container to define an elevated pressure fluid curtain in the form of a dynamic fluid barrier, channeled within a multi-walled isolation device barrier space between the said first and said second containers; an elevated pressure fluid curtain in the form of a dynamic fluid barrier defined by density, molecular weight, phase, fluid viscosity, temperature, pressure, clarity, a fluid with a density between 0.089 g/l but less than 13.5 g/cm$^3$ is envisioned as preferred, a fluid with a molecular weight between 1.008 g/mole and 200.58 g/mole is envisioned as preferred, a fluid in a gas or liquid phase is envisioned as preferred, a fluid with a viscosity between 8.4×10-6 Pa s but less than 250,000 cP, including both Newtonian and non-Newtonian character, is envisioned as preferred, a fluid with a temperature between 1 degree Kelvin but less than 475 Kelvin is envisioned as preferred, a fluid with a pressure between −30 inches Hg but less than 50 psi is envisioned as preferred, a clear and colorless fluid, capable of being loaded with a color or turbidity marker is envisioned as preferred to facilitate leak location, a first fluid intake duct associated with the said first container, said first fluid intake duct providing fluid communication between said elevated pressure fluid curtain in the form of a dynamic fluid barrier, channeled within a multi-walled isolation device barrier space and said isolation space or, alternatively between the ambient and said isolation space; a second fluid intake duct associated with said second container, said second fluid intake duct providing fluid communication between the ambient and said elevated pressure fluid curtain in the form of a dynamic fluid barrier, channeled within a multi-walled isolation device barrier space; a first intake filter for filtering fluid passing through first intake duct; a second intake filter for filtering fluid passing through second intake duct; a first fluid exhaust duct associated with said first container, said first fluid exhaust duct providing directional fluid communication from said isolation space to said elevated pressure fluid curtain in the form of a dynamic fluid barrier, channeled within a multi-walled isolation device barrier space or, alternatively from said isolation space to the ambient; a second exhaust duct associated with said second container, said second exhaust duct providing directional fluid communication form said barrier space to the ambient; a first exhaust filter for filtering fluid passing through said first exhaust duct; a second exhaust filter for filtering fluid passing through said second exhaust duct; from said isolation space to the ambient; and a first fluid pump associated with at least one of said intake ducts for moving fluid from the ambient to either isolation space and/or said elevated pressure fluid curtain in the form of a dynamic fluid barrier, channeled within a multi-walled isolation device barrier space; and a second fluid pump associated with at least one of said intake ducts for moving fluid from the ambient to either isolation space and/or said elevated pressure fluid curtain in the form of a dynamic fluid barrier, channeled within a multi-walled isolation device barrier space back to the ambient.

2. The elevated pressure fluid curtain in the form of a dynamic fluid barrier, where the pressure within the barrier space is never below ambient, channeled within a multi-walled isolation device according to claim 1, wherein fluid pressure within said isolation space is less then fluid pressure within said elevated pressure fluid curtain in the form of a dynamic fluid barrier, channeled within a multi-walled isolation device barrier space procatively preventing vapors, fumes, gases, particles or isolator atmosphere from entering the barrier space by immediately plugging any breach in the solid barrier with dynamic fluid flow providing the benefit of; a continuously clean barrier space post interior isolator breach, removing the need to immediately clean an otherwise contaminated space between the isolator walls, a continuously safe and operational environment in the ambient while always maintaining an acceptable level of a clean environment immediately adjacent to any breach in an interior isolator wall, a continuous aseptic environment for the continuous operation or controlled shut down of an aseptic operation within the isolator such as an aseptic vial filling procedure.

3. The elevated pressure fluid curtain in the form of a dynamic fluid barrier, channeled within a multi-walled isolation device according to claim 1, further comprising a control means in electronic communication with said intake ducts, said exhaust ducts and said fluid pumps for independently regulating fluid pressures within said isolation space and within said elevated pressure fluid curtain in the form of a dynamic fluid barrier, channeled within a multi-walled isolation device barrier space each to a desired pressure to maintain a proactive elevated fluid curtain in the form of a dynamic fluid barrier during breach of any of the inner or exterior isolator walls or other enclosure material breaches and simultaneously preventing entry to the barrier space by contaminants in the ambient or aseptic potent compounds contained within the primary isolator.

4. The elevated pressure fluid curtain in the form of a dynamic fluid barrier, channeled within a multi-walled isolation device according to claim 3, further comprising a flow splitter, permitting a single perforation simultaneously into the interior and exterior isolator shell materials, electronically connected to an under the control of said control means, and flow splitter communicating with said first fluid pump for dividing the fluid forced by said first fluid pump between each intake duct thereby maintaining the desired independent pressures within said elevated pressure fluid curtain in the form of a dynamic fluid barrier, channeled within a multi-walled isolation device barrier space and within said isolation space.

5. The elevated pressure fluid curtain in the form of a dynamic fluid barrier, channeled within a multi-walled isolation device according to claim 3, further comprising a flow combiner, permitting a single perforation simultaneously into the interior and exterior isolator shell materials, electronically connected to and under the control of said control means, said flow combiner communicating with said second fluid pump for combining the fluid forced by said second fluid pump from each exhaust duct thereby further assisting in regulating the desired independent pressures within said elevated pressure fluid curtain in the form of a dynamic fluid barrier, channeled within a multi-walled isolation device barrier space and within said isolation space.

* * * * *